United States Patent
Almo et al.

(10) Patent No.: US 10,717,776 B2
(45) Date of Patent: Jul. 21, 2020

(54) TUMOR NECROSIS FACTOR 1B (TNF-1B) MUTANTS AND METHODS OF USE THEREOF TO SCREEN FOR CANDIDATE THERAPEUTIC COMPOUNDS

(71) Applicant: ALBERT EINSTEIN COLLEGE OF MEDICINE, Bronx, NY (US)

(72) Inventors: Steven C. Almo, Pelham, NY (US); Sarah Garrett-Thomson, New York, NY (US); Ron Seidel, Larchmont, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 15/945,887

(22) Filed: Apr. 5, 2018

(65) Prior Publication Data
US 2018/0273604 A1 Sep. 27, 2018

Related U.S. Application Data

(63) Continuation-in-part of application No. PCT/US2016/057469, filed on Oct. 18, 2016.

(60) Provisional application No. 62/243,688, filed on Oct. 20, 2015.

(51) Int. Cl.
| | |
|---|---|
| *C07K 14/705* | (2006.01) |
| *G01N 33/68* | (2006.01) |
| *C07K 14/715* | (2006.01) |
| *G01N 33/50* | (2006.01) |
| *A61K 38/00* | (2006.01) |

(52) U.S. Cl.
CPC .... *C07K 14/70578* (2013.01); *C07K 14/7151* (2013.01); *G01N 33/5008* (2013.01); *G01N 33/6863* (2013.01); *A61K 38/00* (2013.01); *C07K 2319/30* (2013.01); *G01N 2333/525* (2013.01); *G01N 2333/70575* (2013.01); *G01N 2500/04* (2013.01)

(58) Field of Classification Search
CPC .......... C07K 14/70578; C07K 14/7151; C07K 2319/30; G01N 33/5008; G01N 33/6863; G01N 2333/525; G01N 2333/70575; G01N 2500/04; A61K 38/00
See application file for complete search history.

(56) References Cited

U.S. PATENT DOCUMENTS

| | | | |
|---|---|---|---|
| 2008/0176796 A1 | 7/2008 | Bradley et al. | |
| 2010/0150841 A1 | 6/2010 | Goukassian et al. | |

FOREIGN PATENT DOCUMENTS

| | | |
|---|---|---|
| WO | 2006074370 A2 | 7/2006 |
| WO | 2010151671 A2 | 12/2010 |

OTHER PUBLICATIONS

PCT International Search Report and Written Opinion dated Jan. 24, 2017 for PCT International Patent Application PCT/US2016/057469, 10 pages.
Faustman D et al., entitled "TNF receptor 2 pathway: drug target for autoimmune diseases," Nat Rev Drug Discov, May 21, 2010, vol. 9, pp. 482-493.
Arihiro S, et al. "Differential expression of mucosal addressin cell adhesion molecule-1 (MadCAM-1) in ulcerative colitis and Crohn's disease" Pathology International 2002, 52(5-6):367-374.
Fu T, et al. "The ICOS/ICOSL pathway is required for optimal antitumor responses mediated by anti-CTLA-4 therapy" Cancer Research 2011, 71(16):5445-5454.
Hamel KM, et al. "B cell-specific expression of inducible costimulator ligand is necessary for the induction of arthritis in mice" Arthritis & Rheumatology 2014, 66(1):60-67.
Hedl M, et al. "Pattern recognition receptor signaling in human dendritic cells is enhanced by ICOS ligand and modulated by the Crohn's disease ICOSLG risk allele" Immunity 2014, 40(5):734-746.
Liu D, et al. "T-B-cell entanglement and ICOSL-driven feedforward regulation of germinal centre reaction" Nature 2015, 517(7533):214-218.
Nelson MH, et a. The Inducible Costimulator Augments Tc17 Cell Responses to Self and Tumor Tissue. Journal of Immunology 2015, 194:1737-1747.
Pan XC, et al. "Further study of anti-ICOS immunotherapy for rat cardiac allograft rejection" Surgery Today 2008, 38(9):815-825.
Richter G, et al. "Tumor necrosis factor-alpha regulates the expression of inducible costimulator receptor ligand on CD34(+) progenitor cells during differentiation into antigen presenting cells" The Journal of Biological Chemistry 2001, 276(49):45686-45693.
Sandborn WJ, et al. Etanercept for active Crohn's disease: a randomized, double-blind, placebo-controlled trial. Gastroenterology 2001, 121(5): 1088-1094.
Ueha S, et al. "Intervention of MadCAM-1 or fractalkine alleviates graft-versus-host reaction associated intestinal injury while preserving graft-versus-tumor effects" Journal of Leukocyte Biology 2007, 81(1): 176-185.
Xin L, et al. Commensal microbes drive intestinal inflammation by IL-17-producing CD4+ T cells through ICOSL and OX40L costimulation in the absence of B7-l and B7-2. Proceedings of the National Academy of Sciences of the United States of America 2014, 111(29):10672-10677.
Yao S, et al. "B7-h2 is a costimulatory ligand for CD28 in human" Immunity 2011, 34(5):729-740.
NCBI GenBank, GenPept tumor necrosis factor receptor superfamily member 1B precursor [*Homo sapiens*] NCBI Reference Sequence: NP_001057.1, Sep. 9, 2016, 3 pages.

*Primary Examiner* — Robert S Landsman
(74) *Attorney, Agent, or Firm* — Perkins Coie LLP

(57) ABSTRACT

Disclosed are tumor necrosis factor receptor 1B (TNFR-1B) signaling targets and TNFR-1B mutants and their uses for treatment of diseases and disorders.

12 Claims, 20 Drawing Sheets
Specification includes a Sequence Listing.

SEQUENCE LISTING

<160> NUMBER OF SEQ ID NOS: 4

<210> SEQ ID NO 1
<211> LENGTH: 1485
<212> TYPE: DNA
<213> ORGANISM: Artificial Sequence
<220> FEATURE:
<223> OTHER INFORMATION: TNFR-1B Fc fusion protein
<220> FEATURE:
<221> NAME/KEY: CDS
<222> LOCATION: (1)..(1485)

<400> SEQUENCE: 1

```
atg ggc gtg cac gag tgc ccc gcc tgg ctg tgg ctg ctg ctg agc ctg      48
Met Gly Val His Glu Cys Pro Ala Trp Leu Trp Leu Leu Leu Ser Leu
1               5                   10                  15 ctg agt cta cct ctc ggc ctg cct gtg cta ggc ttg ccc gcc cag gtg      96
Leu Ser Leu Pro Leu Gly Leu Pro Val Leu Gly Leu Pro Ala Gln Val
            20                  25                  30 gca ttt aca ccc tac gcc ccg gag ccc ggg agc aca tgc cgg ctc aga     144
Ala Phe Thr Pro Tyr Ala Pro Glu Pro Gly Ser Thr Cys Arg Leu Arg
        35                  40                  45 gaa tac tat gac cag aca gct cag atg tgc tgc agc aaa tgc tcg ccg     192
Glu Tyr Tyr Asp Gln Thr Ala Gln Met Cys Cys Ser Lys Cys Ser Pro
    50                  55                  60 ggc caa cat gca aaa gtc ttc tgt acc aag acc tcg gac acc gtg tgt     240
Gly Gln His Ala Lys Val Phe Cys Thr Lys Thr Ser Asp Thr Val Cys
65                  70                  75                  80 gac tcc tgt gag gac agc aca tac acc cag ctc tgg aac tgg gtt ccc     288
Asp Ser Cys Glu Asp Ser Thr Tyr Thr Gln Leu Trp Asn Trp Val Pro
                85                  90                  95 gag tgc ttg agc tgt ggc tcc cgc tgt agc tct gac cag gtg gaa act     336
Glu Cys Leu Ser Cys Gly Ser Arg Cys Ser Ser Asp Gln Val Glu Thr
            100                 105                 110
```

-continued

| | | |
|---|---|---|
| caa gcc tgc act cgg gaa cag aac cgc atc tgc acc tgc agg ccc ggc<br>Gln Ala Cys Thr Arg Glu Gln Asn Arg Ile Cys Thr Cys Arg Pro Gly<br>      115                  120                  125 | 384 | |
| tgg tac tgc gcg ctg agc aag cag gag ggg tgc cgg ctg tgc gcg ccg<br>Trp Tyr Cys Ala Leu Ser Lys Gln Glu Gly Cys Arg Leu Cys Ala Pro<br>130                  135                  140 | 432 | |
| ctg cgc aag tgc cgc ccg ggc ttc ggc gtg gcc aga cca gga act gaa<br>Leu Arg Lys Cys Arg Pro Gly Phe Gly Val Ala Arg Pro Gly Thr Glu<br>145                  150                  155                  160 | 480 | |
| aca tca gac gtg gtg tgc aag ccc tgt gcc ccg ggg acg ttc tcc aac<br>Thr Ser Asp Val Val Cys Lys Pro Cys Ala Pro Gly Thr Phe Ser Asn<br>                  165                  170                  175 | 528 | |
| acg act tca tcc acg gat att tgc agg ccc cac cag atc tgt aac gtg<br>Thr Thr Ser Ser Thr Asp Ile Cys Arg Pro His Gln Ile Cys Asn Val<br>                      180                  185                  190 | 576 | |
| gtg gcc atc cct ggg aat gca agc atg gat gca gtc tgc acg tcc acg<br>Val Ala Ile Pro Gly Asn Ala Ser Met Asp Ala Val Cys Thr Ser Thr<br>                  195                  200                  205 | 624 | |
| tcc ccc acc cgg agt atg gcc cca ggg gca gta cac tta ccc cag cca<br>Ser Pro Thr Arg Ser Met Ala Pro Gly Ala Val His Leu Pro Gln Pro<br>210                  215                  220 | 672 | |
| gtg tcc aca cga tcc caa cac acg cag cca act cca gaa ccc agc act<br>Val Ser Thr Arg Ser Gln His Thr Gln Pro Thr Pro Glu Pro Ser Thr<br>225                  230                  235                  240 | 720 | |
| gct cca agc acc tcc ttc ctg ctc cca atg ggc ccc agc ccc cca gct<br>Ala Pro Ser Thr Ser Phe Leu Leu Pro Met Gly Pro Ser Pro Pro Ala<br>                  245                  250                  255 | 768 | |
| gaa ggg agc act ggc gac gag ccc aaa tct tgt gac aaa act cac aca<br>Glu Gly Ser Thr Gly Asp Glu Pro Lys Ser Cys Asp Lys Thr His Thr<br>                      260                  265                  270 | 816 | |
| tgc cca ccg tgc cca gca cct gaa ctc ctg ggg gga ccg tca gtc ttc<br>Cys Pro Pro Cys Pro Ala Pro Glu Leu Leu Gly Gly Pro Ser Val Phe<br>275                  280                  285 | 864 | |
| ctc ttc ccc cca aaa ccc aag gac acc ctc atg atc tcc cgg acc cct<br>Leu Phe Pro Pro Lys Pro Lys Asp Thr Leu Met Ile Ser Arg Thr Pro<br>                  290                  295                  300 | 912 | |
| gag gtc aca tgc gtg gtg gtg gac gtg agc cac gaa gac cct gag gtc<br>Glu Val Thr Cys Val Val Val Asp Val Ser His Glu Asp Pro Glu Val<br>305                  310                  315                  320 | 960 | |
| aag ttc aac tgg tac gtg gac ggc gtg gag gtg cat aat gcc aag aca<br>Lys Phe Asn Trp Tyr Val Asp Gly Val Glu Val His Asn Ala Lys Thr<br>                  325                  330                  335 | 1008 | |
| aag ccg cgg gag gag cag tac aac agc acg tac cgt gtg gtc agc gtc<br>Lys Pro Arg Glu Glu Gln Tyr Asn Ser Thr Tyr Arg Val Val Ser Val<br>                      340                  345                  350 | 1056 | |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys<br>                  355                  360                  365 | 1104 | |
| aag gtc tcc aac aaa gcc ctc cca gcc ccc atc gag aaa acc atc tcc<br>Lys Val Ser Asn Lys Ala Leu Pro Ala Pro Ile Glu Lys Thr Ile Ser<br>370                  375                  380 | 1152 | |
| aaa gcc aaa ggg cag ccc cga gaa cca cag gtg tac acc ctg ccc cca<br>Lys Ala Lys Gly Gln Pro Arg Glu Pro Gln Val Tyr Thr Leu Pro Pro<br>385                  390                  395                  400 | 1200 | |
| tcc cgg gag gag atg acc aag aac cag gtc agc ctg acc tgc ctg gtc<br>Ser Arg Glu Glu Met Thr Lys Asn Gln Val Ser Leu Thr Cys Leu Val<br>                  405                  410                  415 | 1248 | |
| aaa ggc ttc tat ccc agc gac atc gcc gtg gag tgg gag agc aat ggg<br>Lys Gly Phe Tyr Pro Ser Asp Ile Ala Val Glu Trp Glu Ser Asn Gly | 1296 | |

```
                420             425             430
cag ccg gag aac aac tac aag acc acg cct ccc gtg ctg gac tcc gac      1344
Gln Pro Glu Asn Asn Tyr Lys Thr Thr Pro Pro Val Leu Asp Ser Asp
        435                 440                 445 ggc tcc ttc ttc ctc tat agc aag ctc acc gtg gac aag agc agg tgg      1392
Gly Ser Phe Phe Leu Tyr Ser Lys Leu Thr Val Asp Lys Ser Arg Trp
450                 455                 460 cag cag ggg aac gtc ttc tca tgc tcc gtg atg cat gag gct ctg cac      1440
Gln Gln Gly Asn Val Phe Ser Cys Ser Val Met His Glu Ala Leu His
465                 470                 475                 480 aac cac tac acg cag aag agc ctc tcc ctg tcc ccg ggt aaa tag          1485
Asn His Tyr Thr Gln Lys Ser Leu Ser Leu Ser Pro Gly Lys
                485                 490

<210> SEQ ID NO 2
<211> LENGTH: 494
<212> TYPE: PRT
<213> ORGANISM: Artificial Sequence
<220> FEATURE:
<223> OTHER INFORMATION: TNFR-1B Fc fusion protein
<220> FEATURE:
<221> NAME/KEY: MISC_FEATURE
<222> LOCATION: (28)..(262)
<223> OTHER INFORMATION: Corresponds to AAs 23-257 of TNFR-1B (SEQ ID
      NO:4)
<220> FEATURE:
<221> NAME/KEY: MISC_FEATURE
<222> LOCATION: (263)..(494)
<223> OTHER INFORMATION: Fc IgG1 heavy chain constant region (GenBank
      AEV43323.1)
<300> PUBLICATION INFORMATION:
<308> DATABASE ACCESSION NUMBER: GenBank AEV43323.1
<309> DATABASE ENTRY DATE: 2016-07-25
<313> RELEVANT RESIDUES IN SEQ ID NO: (263)..(494)

<400> SEQUENCE: 2

Met Gly Val His Glu Cys Pro Ala Trp Leu Trp Leu Leu Leu Ser Leu
1               5                   10                  15

Leu Ser Leu Pro Leu Gly Leu Pro Val Leu Gly Leu Pro Ala Gln Val
                20                  25                  30

Ala Phe Thr Pro Tyr Ala Pro Glu Pro Gly Ser Thr Cys Arg Leu Arg
            35                  40                  45

Glu Tyr Tyr Asp Gln Thr Ala Gln Met Cys Cys Ser Lys Cys Ser Pro
        50                  55                  60

Gly Gln His Ala Lys Val Phe Cys Thr Lys Thr Ser Asp Thr Val Cys
65                  70                  75                  80

Asp Ser Cys Glu Asp Ser Thr Tyr Thr Gln Leu Trp Asn Trp Val Pro
                85                  90                  95

Glu Cys Leu Ser Cys Gly Ser Arg Cys Ser Ser Asp Gln Val Glu Thr
            100                 105                 110

Gln Ala Cys Thr Arg Glu Gln Asn Arg Ile Cys Thr Cys Arg Pro Gly
        115                 120                 125

Trp Tyr Cys Ala Leu Ser Lys Gln Glu Gly Cys Arg Leu Cys Ala Pro
130                 135                 140

Leu Arg Lys Cys Arg Pro Gly Phe Gly Val Ala Arg Pro Gly Thr Glu
145                 150                 155                 160

Thr Ser Asp Val Val Cys Lys Pro Cys Ala Pro Gly Thr Phe Ser Asn
                165                 170                 175

Thr Thr Ser Ser Thr Asp Ile Cys Arg Pro His Gln Ile Cys Asn Val
            180                 185                 190

Val Ala Ile Pro Gly Asn Ala Ser Met Asp Ala Val Cys Thr Ser Thr
```

```
                  195                 200                 205

Ser Pro Thr Arg Ser Met Ala Pro Gly Ala Val His Leu Pro Gln Pro
    210                 215                 220

Val Ser Thr Arg Ser Gln His Thr Gln Pro Thr Pro Glu Pro Ser Thr
225                 230                 235                 240

Ala Pro Ser Thr Ser Phe Leu Leu Pro Met Gly Pro Ser Pro Pro Ala
                245                 250                 255

Glu Gly Ser Thr Gly Asp Glu Pro Lys Ser Cys Asp Lys Thr His Thr
            260                 265                 270

Cys Pro Pro Cys Pro Ala Pro Glu Leu Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490

<210> SEQ ID NO 3
<211> LENGTH: 1431
<212> TYPE: DNA
<213> ORGANISM: Artificial Sequence
<220> FEATURE:
<223> OTHER INFORMATION: TNFR-1B construct
<220> FEATURE:
<221> NAME/KEY: misc_feature
<222> LOCATION: (4)..(789)
<223> OTHER INFORMATION: Encodes AAs 1-262 of TNFR-1B Fc fusion protein
      (SEQ ID NO:2)
<220> FEATURE:
<221> NAME/KEY: misc_feature
<222> LOCATION: (85)..(1401)
<223> OTHER INFORMATION: Encodes AAs 23-461 of TNFR-1B (SEQ ID NO:4)

<400> SEQUENCE: 3
accatgggcg tgcacgagtg ccccgcctgg ctgtggctgc tgctgagcct gctgagtcta      60
cctctcggcc tgcctgtgct aggcttgccc gcccaggtgg catttacacc ctacgccccg     120
```

```
gagcccggga gcacatgccg gctcagagaa tactatgacc agacagctca gatgtgctgc    180
agcaaatgct cgccgggcca acatgcaaaa gtcttctgta ccaagacctc ggacaccgtg    240
tgtgactcct gtgaggacag cacatacacc cagctctgga actgggttcc cgagtgcttg    300
agctgtggct cccgctgtag ctctgaccag gtggaaactc aagcctgcac tcgggaacag    360
aaccgcatct gcacctgcag gcccggctgg tactgcgcgc tgagcaagca ggaggggtgc    420
cggctgtgcg cgccgctgcg caagtgccgc ccgggcttcg gcgtggccag accaggaact    480
gaaacatcag acgtggtgtg caagccctgt gccccgggga cgttctccaa cacgacttca    540
tccacggata tttgcaggcc ccaccagatc tgtaacgtgg tggccatccc tgggaatgca    600
agcatggatg cagtctgcac gtccacgtcc cccacccgga gtatggcccc aggggcagta    660
cacttacccc agccagtgtc cacacgatcc aacacacgc agccaactcc agaacccagc    720
actgctccaa gcacctcctt cctgctccca atgggcccca gcccccagc tgaagggagc    780 actggcgact tcgctcttcc agttggactg attgtgggtg tgacagcctt gggtctacta    840
ataataggag tggtgaactg tgtcatcatg acccaggtga aaagaagcc cttgtgcctg    900 cagagagaag ccaaggtgcc tcacttgcct gccgataagg cccggggtac acagggcccc    960
gagcagcagc acctgctgat cacagcgccg agctccagca gcagctccct ggagagctcg    1020
gccagtgcgt tggacagaag ggcgcccact cggaaccagc cacaggcacc aggcgtggag    1080
gccagtgggg ccggggaggc ccgggccagc accgggagct cagattcttc ccctggtggc    1140
catgggaccc aggtcaatgt cacctgcatc gtgaacgtct gtagcagctc tgaccacagc    1200
tcacagtgct cctcccaagc cagctccaca atggagacac agattccag ccctcggag    1260 tccccgaagg acgagcaggt ccccttctcc aaggaggaat gtgcctttcg gtcacagctg    1320
gagacgccag agaccctgct ggggagcacc gaagagaagc ccctgcccct ggagtgcct    1380 gatgctggga tgaagcccag tggtggcgga agcgagaacc tgtactccag t            1431
```

<210> SEQ ID NO 4
<211> LENGTH: 461
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: Signal peptide
<300> PUBLICATION INFORMATION:
<308> DATABASE ACCESSION NUMBER: NCBI NP_001057.1
<309> DATABASE ENTRY DATE: 2016-09-09
<313> RELEVANT RESIDUES IN SEQ ID NO: (1)..(461)

<400> SEQUENCE: 4

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
```

```
            100             105                 110
Glu Gln Asn Arg Ile Cys Thr Cys Arg Pro Gly Trp Tyr Cys Ala Leu
            115                 120                 125
Ser Lys Gln Glu Gly Cys Arg Leu Cys Ala Pro Leu Arg Lys Cys Arg
    130                 135                 140
Pro Gly Phe Gly Val Ala Arg Pro Gly Thr Glu Thr Ser Asp Val Val
145                 150                 155                 160
Cys Lys Pro Cys Ala Pro Gly Thr Phe Ser Asn Thr Thr Ser Ser Thr
                165                 170                 175
Asp Ile Cys Arg Pro His Gln Ile Cys Asn Val Val Ala Ile Pro Gly
            180                 185                 190
Asn Ala Ser Met Asp Ala Val Cys Thr Ser Thr Ser Pro Thr Arg Ser
        195                 200                 205
Met Ala Pro Gly Ala Val His Leu Pro Gln Pro Val Ser Thr Arg Ser
    210                 215                 220
Gln His Thr Gln Pro Thr Pro Glu Pro Ser Thr Ala Pro Ser Thr Ser
225                 230                 235                 240
Phe Leu Leu Pro Met Gly Pro Ser Pro Pro Ala Glu Gly Ser Thr Gly
                245                 250                 255
Asp Phe Ala Leu Pro Val Gly Leu Ile Val Gly Val Thr Ala Leu Gly
            260                 265                 270
Leu Leu Ile Ile Gly Val Val Asn Cys Val Ile Met Thr Gln Val Lys
        275                 280                 285
Lys Lys Pro Leu Cys Leu Gln Arg Glu Ala Lys Val Pro His Leu Pro
    290                 295                 300
Ala Asp Lys Ala Arg Gly Thr Gln Gly Pro Glu Gln Gln His Leu Leu
305                 310                 315                 320
Ile Thr Ala Pro Ser Ser Ser Ser Ser Ser Leu Glu Ser Ser Ala Ser
                325                 330                 335
Ala Leu Asp Arg Arg Ala Pro Thr Arg Asn Gln Pro Gln Ala Pro Gly
            340                 345                 350
Val Glu Ala Ser Gly Ala Gly Glu Ala Arg Ala Ser Thr Gly Ser Ser
        355                 360                 365
Asp Ser Ser Pro Gly Gly His Gly Thr Gln Val Asn Val Thr Cys Ile
    370                 375                 380
Val Asn Val Cys Ser Ser Ser Asp His Ser Ser Gln Cys Ser Ser Gln
385                 390                 395                 400
Ala Ser Ser Thr Met Gly Asp Thr Asp Ser Ser Pro Ser Glu Ser Pro
                405                 410                 415
Lys Asp Glu Gln Val Pro Phe Ser Lys Glu Glu Cys Ala Phe Arg Ser
            420                 425                 430
Gln Leu Glu Thr Pro Glu Thr Leu Leu Gly Ser Thr Glu Glu Lys Pro
        435                 440                 445
Leu Pro Leu Gly Val Pro Asp Ala Gly Met Lys Pro Ser
    450                 455                 460
```

US 10,717,776 B2

TUMOR NECROSIS FACTOR 1B (TNF-1B) MUTANTS AND METHODS OF USE THEREOF TO SCREEN FOR CANDIDATE THERAPEUTIC COMPOUNDS

CROSS-REFERENCE TO RELATED APPLICATIONS

This application is a continuation-in-part of and claims priority of PCT International Patent Application No. PCT/US2016/057469, filed Oct. 18, 2016, which published as PCT Publ. No. WO2017/070076 on Apr. 27, 2017, and which designates the United States of America and claims the benefit of U.S. Provisional Patent Application No. 62/243,688, filed on Oct. 20, 2015, the contents of which are herein incorporated by reference in their entirety into the present application.

STATEMENT OF GOVERNMENT SUPPORT

This invention was made with government support under grant numbers GM094662 and GM094665 awarded by the National Institutes of Health. The government has certain rights in the invention.

BACKGROUND OF THE INVENTION

Throughout this application various publications are referred to in brackets. Full citations for these references may be found at the end of the specification. The disclosures of these publications are hereby incorporated by reference in their entirety into the subject application to more fully describe the art to which the subject invention pertains.

The present invention addresses the need for improved compounds for treating diseases or disorders such as rheumatoid arthritis, psoriatic arthritis, ankylosing spondylitis, plaque psoriasis, juvenile idiopathic arthritis, inflammation, Crohn's disease, ulcerative colitis, inflammatory bowel disease, and other autoimmune and inflammatory diseases.

SUMMARY OF THE INVENTION

Methods are provided for screening for a candidate compound for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis, inflammatory bowel disease and inflammatory disease, the methods comprising testing the compound to determine if the compound modulates the interaction between one or more of TNFR-1B and ICOS-L, TNFR-1B and MadCAM-1, TNFR-1B and ISLR2, and B7-1 and ISLR2, wherein a compound that is tested and determined to modulate the interaction between one or more of TNFR-1B and ICOS-L, TNFR-1B and MadCAM-1, TNFR-1B and ISLR2, and B7-1 and ISLR2 is a candidate compound for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis, inflammatory bowel disease and inflammatory disease.

Methods are also provided for screening for a candidate compound for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis and inflammatory bowel disease, the methods comprising testing a modified TNFR-1B compound or mutant to determine if the modified TNFR-1B compound or mutant has modified binding affinity and/or selectivity for one or more of ICOS-L, MadCAM-1 and ISLR2, wherein a modified TNFR-1B compound or mutant that is tested and determined to have modified binding affinity and/or selectivity for one or more of ICOS-L, MadCAM-1 and ISLR2 is a candidate compound or mutant for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis and inflammatory bowel disease.

Also provided are mutants of TNFR-1B that modulate the binding of TNFR-1B to one or more of TNFα, ICOS-L and MadCAM-1.

DETAILED DESCRIPTION OF THE INVENTION

Figure 1A:
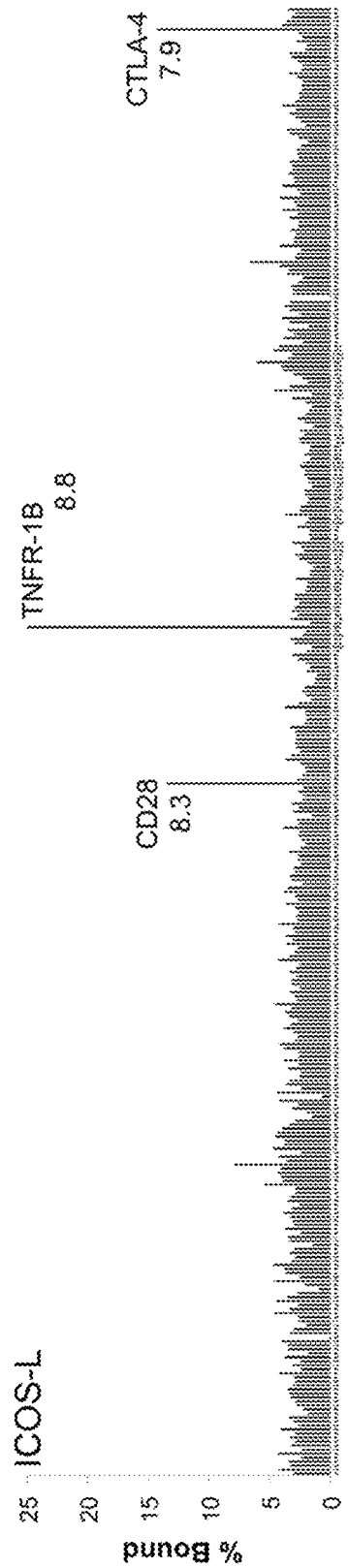
FIG. 1A. Identification of TNFR-1B ligands in a cell-cell based screen against Ig and TNFR superfamily members. Cells expressing ICOS-L were used to challenge a library consisting of ~400 Ig and TNFR superfamily members expressed as GFP fusions. Cell-cell complexes were analyzed by flow cytometery and the percent bound (GFP/mCherry double positive events divided by the total number of cells) was determined across all 400 targets. The numbers below each gene name are the statistical Z-scores, with a Z-score of 2.8 being equivalent to a P-value of 0.005. Z-scores were calculated by determining the average ($\mu$) and std dev ($\sigma$) for the % bound across each 96-well plate and using the formula Abs $z=(x-\mu)/\sigma$. Besides two known receptors of ICOS-L, namely CD28 and CTLA-4, an additional interaction with TNFR-1B was identified.

The present invention provides a method for screening for a candidate compound for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis and inflammatory bowel disease, the method comprising testing the compound to determine if the compound modulates the interaction between one or more of TNFR-1B and ICOS-L, TNFR-1B and MadCAM-1, TNFR-1B and ISLR2, and B7-1 and ISLR2, wherein a compound that is tested and determined to modulate the interaction between one or more of TNFR-1B and ICOS-L, TNFR-1B and MadCAM-1, TNFR-1B and ISLR2, and B7-1 and ISLR2 is a candidate compound for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis and inflammatory bowel disease.

Binding between TNFR-1B and ICOS-L, TNFR-1B and MadCAM-1, TNFR-1B and ISLR2, and/or B7-1 and ISLR2 can be determined in the presence of the candidate compound and in the absence of the candidate compound, where a change in the binding between TNFR-1B and ICOS-L, TNFR-1B and MadCAM-1, TNFR-1B and ISLR2, and/or B7-1 and ISLR2 in the presence of the candidate compound indicates that the candidate compound modulates the interaction between TNFR-1B and ICOS-L, TNFR-1B and MadCAM-1, TNFR-1B and ISLR2, and/or B7-1 and ISLR2.

The compound can be, for example, a non-naturally occurring small molecule of 2,000 daltons or less, or an antibody or an antibody fragment.

Also provided is a method for screening for a candidate compound for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis and inflammatory bowel disease, the method comprising testing a modified TNFR-1B compound or mutant to determine if the modified TNFR-1B compound or mutant has modified binding affinity for one or more of ICOS-L, MadCAM-1 and ISLR2, wherein a modified TNFR-1B compound or mutant that is tested and determined to have modified binding affinity for one or more of ICOS-L, MadCAM-1 and ISLR2 is a candidate compound for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis and inflammatory bowel disease.

In some embodiments, the modified TNFR-1B compound or mutant recognizes TNF-alpha, but not one or more of ICOS-L, MadCAM-1 and ISLR2. In some embodiments, the modified TNFR-1B compound or mutant recognizes ICOS-L, but not one or more of TNF-alpha, MadCAM-1 and ISLR2. In some embodiments, the modified TNFR-1B compound or mutant recognizes MadCAM-1, but not one or more of TNF-alpha, ICOS-L, and ISLR2. In some embodiments, the modified TNFR-1B compound or mutant recognizes ISLR2, but not one or more of TNF-alpha, ICOS-L, and MadCAM-1. In some embodiments, the modified TNFR-1B compound or mutant recognizes ICOS-L and MadCAM-1, but not TNF-alpha or ISLR2. In some embodiments, the compound or mutant has enhanced affinities for all ligands compared to TNFR-1B. In some embodiments, the compound or mutant has enhanced affinities for some ligands compared to TNFR-1B. In some embodiments, the compound or mutant has reduced affinities for some ligands compared to TNFR-1B. In some embodiments, the compound or mutant has enhanced affinities for some ligands compared to TNFR-1B and reduced affinities for some ligands compared to TNFR-1B. In some embodiments, the compound or mutant recognizes only one ligand.

In one embodiment, the fusion protein that links the protein for tumor necrosis factor (TNF) receptor 1B (TNFR-1B) to the protein for Immunoglobulin (Ig)G1 Fc is encoded by the following nucleic acid sequence:

```
                                        (SEQ ID NO: 1)
ATGGGCGTGCACGAGTGCCCCGCCTGGCTGTGGCTGCTGCTGAGCCTG

CTGAGTCTACCTCTCGGCCTGCCTGTGCTAGGCTTGCCCGCCCAGGTG

GCATTTACACCCTACGCCCCGGAGCCCGGGAGCACATGCCGGCTCAGA

GAATACTATGACCAGACAGCTCAGATGTGCTGCAGCAAATGCTCGCCG

GGCCAACATGCAAAAGTCTTCTGTACCAAGACCTCGGACACCGTGTGT

GACTCCTGTGAGGACAGCACATACACCCAGCTCTGGAACTGGGTTCCC

GAGTGCTTGAGCTGTGGCTCCCGCTGTAGCTCTGACCAGGTGGAAACT

CAAGCCTGCACTCGGGAACAGAACCGCATCTGCACCTGCAGGCCCGGC

TGGTACTGCGCGCTGAGCAAGCAGGAGGGGTGCCGGCTGTGCGCGCCG

CTGCGCAAGTGCCGCCCGGGCTTCGGCGTGGCCAGACCAGGAACTGAA

ACATCAGACGTGGTGTGCAAGCCCTGTGCCCCGGGGACGTTCTCCAAC

ACGACTTCATCCACGGATATTTGCAGGCCCCACCAGATCTGTAACGTG

GTGGCCATCCCTGGGAATGCAAGCATGGATGCAGTCTGCACGTCCACG

TCCCCCACCCGGAGTATGGCCCCAGGGGCAGTACACTTACCCCAGCCA

GTGTCCACACGATCCCAACACACGCAGCCAACTCCAGAACCCAGCACT

GCTCCAAGCACCTCCTTCCTGCTCCCAATGGGCCCCAGCCCCCCAGCT

GAAGGGAGCACTGGCGACGAGCCCAAATCTTGTGACAAAACTCACACA

TGCCCACCGTGCCCAGCACCTGAACTCCTGGGGGGACCGTCAGTCTTC

CTCTTCCCCCCAAAACCCAAGGACACCCTCATGATCTCCCGGACCCCT

GAGGTCACATGCGTGGTGGTGGACGTGAGCCACGAAGACCCTGAGGTC

AAGTTCAACTGGTACGTGGACGGCGTGGAGGTGCATAATGCCAAGACA

AAGCCGCGGGAGGAGCAGTACAACAGCACGTACCGTGTGGTCAGCGTC

CTCACCGTCCTGCACCAGGACTGGCTGAATGGCAAGGAGTACAAGTGC

AAGGTCTCCAACAAAGCCCTCCCAGCCCCCATCGAGAAAACCATCTCC

AAAGCCAAAGGGCAGCCCCGAGAACCACAGGTGTACACCCTGCCCCCA

TCCCGGGAGGAGATGACCAAGAACCAGGTCAGCCTGACCTGCCTGGTC

AAAGGCTTCTATCCCAGCGACATCGCCGTGGAGTGGGAGAGCAATGGG

CAGCCGGAGAACAACTACAAGACCACGCCTCCCGTGCTGGACTCCGAC

GGCTCCTTCTTCCTCTATAGCAAGCTCACCGTGGACAAGAGCAGGTGG

CAGCAGGGGAACGTCTTCTCATGCTCCGTGATGCATGAGGCTCTGCAC

AACCACTACACGCAGAAGAGCCTCTCCCTGTCCCCGGGTAAATAG.
```

The amino acid sequence of the TNFR-1B Fc fusion encoded by the nucleotide sequence of SEQ ID NO:1 is:

(SEQ ID NO: 2)
MGVHECPAWLWLLLSLLSLPLGLPVLGLPAQVAFTPYAPEPGSTCRLR

EYYDQTAQMCCSKCSPGQHAKVFCTKTSDTVCDSCEDSTYTQLWNWVP

ECLSCGSRCSSDQVETQACTREQNRICTCRPGWYCALSKQEGCRLCAP

LRKCRPGFGVARPGTETSDVVCKPCAPGTFSNTTSSTDICRPHQICNV

VAIPGNASMDAVCTSTSPTRSMAPGAVHLPQPVSTRSQHTQPTPEPST

APSTSFLLPMGPSPPAEGSTGDEPKSCDKTHTCPPCPAPELLGGPSVF

LFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALH

NHYTQKSLSLSPGK.

The nucleic acid sequence of the TNFR-1B construct used as the template for mutagenesis is:

(SEQ ID NO: 3)
ACCATGGGCGTGCACGAGTGCCCCGCCTGGCTGTGGCTGCTGCTGAGC

CTGCTGAGTCTACCTCTCGGCCTGCCTGTGCTAGGCTTGCCCGCCCAG

GTGGCATTTACACCCTACGCCCCGGAGCCCGGGAGCACATGCCGGCTC

AGAGAATACTATGACCAGACAGCTCAGATGTGCTGCAGCAAATGCTCG

CCGGGCCAACATGCAAAAGTCTTCTGTACCAAGACCTCGGACACCGTG

TGTGACTCCTGTGAGGACAGCACATACACCCAGCTCTGGAACTGGGTT

CCCGAGTGCTTGAGCTGTGGCTCCCGCTGTAGCTCTGACCAGGTGGAA

ACTCAAGCCTGCACTCGGGAACAGAACCGCATCTGCACCTGCAGGCCC

GGCTGGTACTGCGCGCTGAGCAAGCAGGAGGGGTGCCGGCTGTGCGCG

CCGCTGCGCAAGTGCCGCCCGGGCTTCGGCGTGGCCAGACCAGGAACT

GAAACATCAGACGTGGTGTGCAAGCCCTGTGCCCCGGGGACGTTCTCC

AACACGACTTCATCCACGGATATTTGCAGGCCCCACCAGATCTGTAAC

GTGGTGGCCATCCCTGGGAATGCAAGCATGGATGCAGTCTGCACGTCC

ACGTCCCCCACCCGGAGTATGGCCCCAGGGGCAGTACACTTACCCCAG

CCAGTGTCCACACGATCCCAACACACGCAGCCAACTCCAGAACCCAGC

ACTGCTCCAAGCACCTCCTTCCTGCTCCCAATGGGCCCCAGCCCCCA

GCTGAAGGGAGCACTGGCGACTTCGCTCTTCCAGTTGGACTGATTGTG

GGTGTGACAGCCTTGGGTCTACTAATAATAGGAGTGGTGAACTGTGTC

ATCATGACCCAGGTGAAAAAGAAGCCCTTGTGCCTGCAGAGAGAAGCC

AAGGTGCCTCACTTGCCTGCCGATAAGGCCCGGGGTACACAGGGCCCC

GAGCAGCAGCACCTGCTGATCACAGCGCCGAGCTCCAGCAGCAGCTCC

CTGGAGAGCTCGGCCAGTGCGTTGGACAGAAGGGCGCCCACTCGGAAC

CAGCCACAGGCACCAGGCGTGGAGGCCAGTGGGGCCGGGAGGCCCGG

GCCAGCACCGGGAGCTCAGATTCTTCCCCTGGTGGCCATGGGACCCAG

-continued
GTCAATGTCACCTGCATCGTGAACGTCTGTAGCAGCTCTGACCACAGC

TCACAGTGCTCCTCCCAAGCCAGCTCCACAATGGGAGACACAGATTCC

AGCCCCTCGGAGTCCCCGAAGGACGAGCAGGTCCCCTTCTCCAAGGAG

GAATGTGCCTTTCGGTCACAGCTGGAGACGCCAGAGACCCTGCTGGGG

AGCACCGAAGAGAAGCCCCTGCCCCTTGGAGTGCCTGATGCTGGGATG

AAGCCCAGTGGTGGCGGAAGCGAGAACCTGTACTCCAGT.

The amino acid sequence of full-length TNFR-1B is:

(SEQ ID NO: 4)
_MAPVAVWAALAVGLELWAAAHAL_PAQVAFTPYAPEPGSTCR

LREYYDQTAQMCCSKCSPGQHAKVFCTKTSDTVCDSCEDSTYTQLWNW

VPECLSCGSRCSSDQVETQACTREQNRICTCRPGWYCALSKQEGCRLC

AOLRKCRPGFGVARPGTETSDVVCKPCAPGTFSNTTSSTDICRPHQIC

NVVAIPGNASMDAVCTSTSPTRSMAPGAVHLPQPVSTRSQHTQPTPEP

STAPSTSFLLPMGPSPPAEGSTGDFALPVGLIVGVTALGLLIIGVVNC

VIMTQVKKKPLCLQREAKVPHLPADKARGTQGPEQQHLLITAPSSSSS

SLESSASALDFRAPTRNQPQAPGVEASGAGEARASTGSSDSSPGGHGT

QVNVTCIVNVCSSSDHSSQCSSQASSTMGDTDSSPSESPKDEQVPFSK

EECAFRSQLETPETLLGSTEEKPLPLGVPDAGMKPS (human,

NCBI Ref. Seq. NP_001057.1) (22 amino acid signal peptide in _bold italics_).

Note that the numbering of the mutagenesis positions starts after removal of the signal peptide. Therefore, position 1=L, position 2=P, position 3=A, etc.

The compound or mutant can also be a candidate for treating any disease or disorder mediated by TNF.

Also provided are mutants of TNFR-1B that modulates the binding of TNFR-1B to one or more of TNFα, ICOS-L and MadCAM-1. Such mutants include, for example, mutants K42D, T48A, N171D, S79D, R113D, L114A, R119D, K120D, D58A, R19D, S59D, L64D, R77A, S107D, R119A, K120A, R129A, V138D, K140A, I156D, I168D, N171A and M174D. Mutants K42D, T48A and N171D, for example, compared to TNFR-1B, have reduced binding to TNFα, ICOS-L and MadCAM-1. Mutants S79D, R113D, L114A, R119D and K120D, for example, compared to TNFR-1B, have reduce binding to ICOS-L and MadCAM-1, but not to TNFα. Mutant D58A, for example, compared to TNFR-1B, has reduced binding to TNFα and ICOS-L, but not to MadCAM-1. Mutants R19D, S59D, L64D, R77A, S107D, R119A, K120A, R129A, V138D, K140A, I156D, I168D, N171A and M174D, for example, compared to TNFR-1B, predominately have reduced binding to MadCAM-1.

Also provided are fusion proteins comprising mutants of TNFR-1B that modulate the binding of TNFR-1B to one or more of TNFα, ICOS-L and MadCAM-1, and an immunoglobulin Fc sequence. In an embodiment, the immunoglobulin is an IgG. In an embodiment, the IgG is an IgG1 or IgG2 or IgG3 or IgG4 or IgM. Preferably, the immunoglobulin is IgG1. Preferably, the Fc domain has the same sequence or 95% or greater sequence identity with a human IgG1 Fc domain. Immunoglobulin Fc sequences are well known in the art. In an embodiment, the term "Fc sequence" herein is used to define a C-terminal region of an immunoglobulin heavy chain, including native sequence Fc regions and variant Fc regions. Although the boundaries of the Fc sequence of an immunoglobulin heavy chain might vary, the human IgG heavy chain Fc is usually defined to stretch from an amino acid residue at position Cys226, or from Pro230, to the carboxyl-terminus thereof. In an embodiment, the C-terminal lysine of the Fc may be removed, for example, during production or purification, or by recombinantly engineering the nucleic acid encoding a heavy chain of the antibody.

In a fusion protein, the presence of the Fc domain markedly increases the plasma half-life of the attached protein, which prolongs therapeutic activity. In addition, the Fc domain also enables the fusion protein to interact with Fc-receptors.

In an embodiment, the Fc domain is linked via a peptide linker that permits flexibility. In an embodiment, the linker is rigid. In an embodiment the linker is cleavable. Non-limiting examples of flexible linkers are Gn, and GGGGS, and (GGGGS)n where n=2, 3, 4 or 5. Non-limiting examples of rigid linkers are (EAAAK)n, (XP)n. Non-limiting examples of cleavable linkers include disulfide links and protease cleavable linkers.

In an embodiment, the fusion protein described herein is recombinantly produced. In an embodiment, the fusion protein is produced in a eukaryotic expression system. In an embodiment, the fusion protein produced in the eukaryotic expression system comprises glycosylation at a residue on the Fc portion.

Also provided are pharmaceutical compositions comprising any of the fusion proteins disclosed herein and a pharmaceutically acceptable carrier. Pharmaceutically acceptable carriers are well known in the art. Pharmaceutically acceptable carriers that can be used herewith encompasses any of the standard pharmaceutical carriers or diluents, such as, for example, a sterile isotonic saline, phosphate buffered saline solution, water, and emulsions, such as an oil/water or water/oil emulsions.

Also provided are methods for treating a subject with a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis and inflammatory bowel disease, the methods comprising administering to the subject any of the fusion proteins disclosed herein in an amount effective to alleviate a sign or symptom of the disease or disorder.

As used herein, to "treat" a disease or disorder means to alleviate or ameliorate or eliminate a sign or symptom of the disease or disorder that is being treated.

Fusion proteins can be administered to subjects using routes of administration known in the art. The administration can be systemic or localized to a specific site. Routes of administration include, but are not limited to, intravenous, intramuscular, intrathecal or subcutaneous injection, and transdermal administration, and injection into a specific site.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specifics discussed are merely illustrative of the invention as described more fully in the claims that follow thereafter.

EXPERIMENTAL DETAILS

Introduction

ENBREL® (etanercept) is a fusion protein that links the protein for tumor necrosis factor (TNF) receptor 1B (TNFR-1B) to the protein for Immunoglobulin (Ig)G1 Fc. ENBREL® (etanercept) is a leading anti-inflammatory drug. This disclosure describes interactions and pathways that are of immediate therapeutic importance and provides strategies for the design of ENBREL® (etanercept) variants with engineered selectivities, which recognize only a subset of its potential ligands, or exhibit increased or reduced affinities for all or subsets of its potential ligands, for the realization of more effective biologics with reduced side effects.

Methods and Results

Figure 1B:
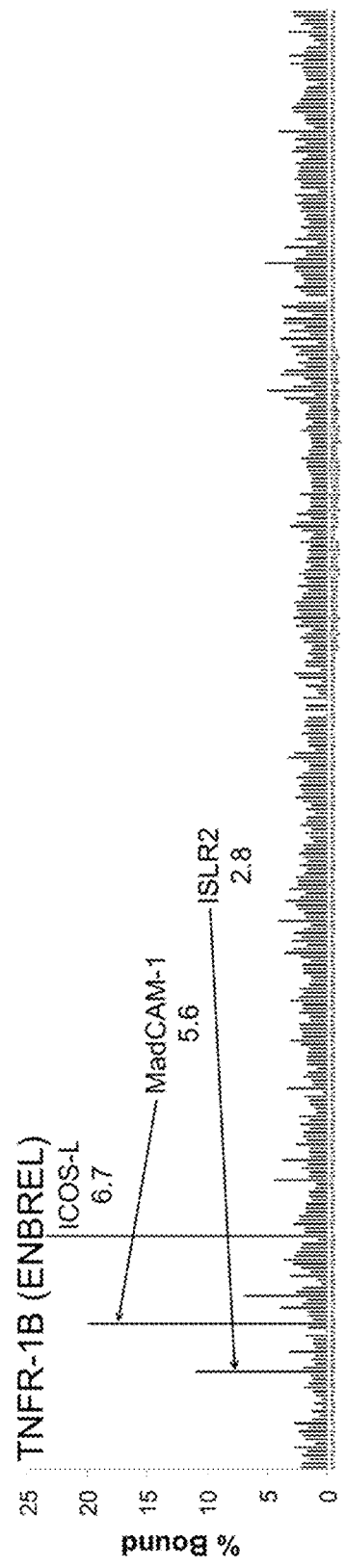
FIG. 1B. Identification of TNFR-1B ligands in a cell-cell based screen against Ig and TNFR superfamily members. Screening the same library as in FIG. 1A with TNFR-1B-mCHERRY expressing cells identified ICOS-L, validating the original screen, as well as two additional interacting proteins, namely MadCAM-1 and ISLR2.
Figure 1C:
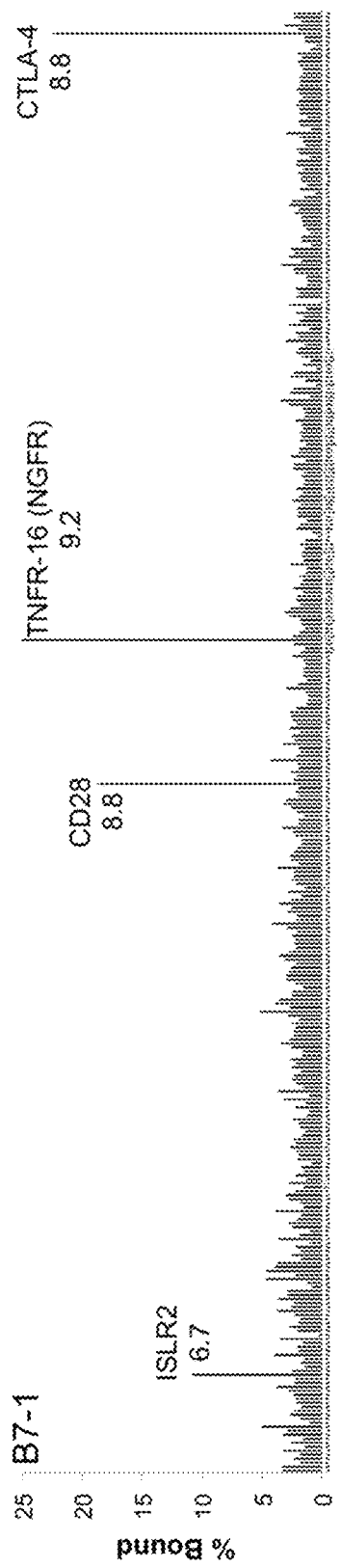
FIG. 1C. Identification of TNFR-1B ligands in a cell-cell based screen against Ig and TNFR superfamily members. Screening with B7-1 expressing cells identified known interactions with CD28, CTLA-4 and NGFR, and an interaction with ISR-L2.
Figure 1D:
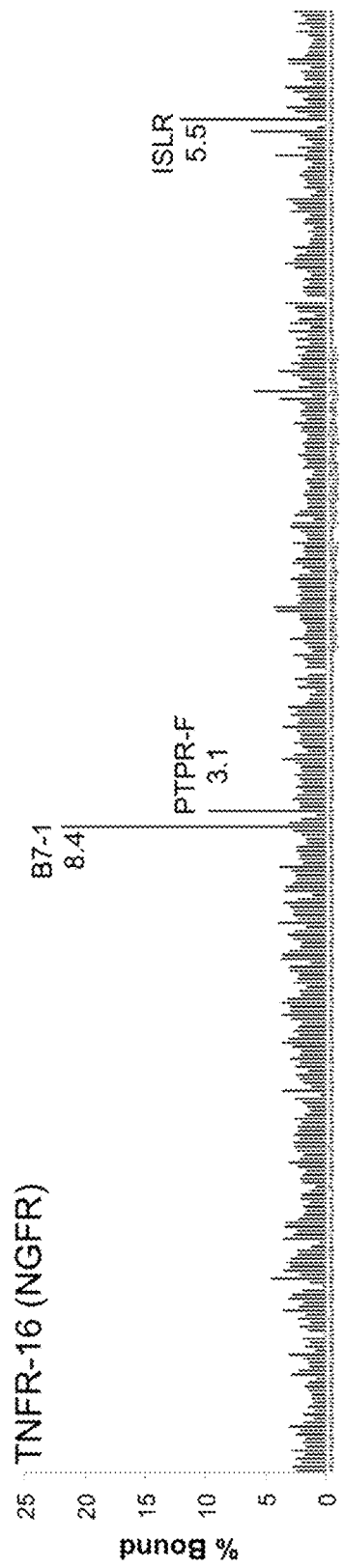
FIG. 1D. Identification of TNFR-1B ligands in a cell-cell based screen against Ig and TNFR superfamily members. Screening with NGFR expressing cells identified the know interaction with B7-1, and interactions with ISLR and PTPR-F.

Data are provided showing results from cell-cell Fluorescence-Activated Cell Sorting (FACS)-based screens utilizing a ~400 member secreted protein library, which contains most members of the human Immunoglobulin (Ig) superfamily and the human Tumor Necrosis Factor Receptor (TNFR) superfamily. In this library, all ectodomains were fused to the mouse PD-L1 transmembrane segment, with covalent linkage to cytoplasmic GFP as a proxy marker for expression. The human erythropoietin (EPO) signal sequence was used to direct secretion of all constructs. These screening efforts revealed a remarkable network of interactions, which demonstrate the coupling of a range of immune and neural regulatory pathways (Table 1). Screening with cells expressing ICOS-L resulted in the identification of two of its known binding partners, CD28 and CTLA-4 [1], as well as a novel interaction with TNFR-1B. Screening the library with cells expressing TNFR-1B resulted in the identification of three novel interacting proteins, ICOS-L, MadCAM-1 and ISLR2 (FIG. 1B), thus validating the TNFR-1B:ICOS-L interaction. The library was also screened with cells expressing MadCAM-1 in which only TNFR-1B was identified (again validating the initial screen, data not shown). Given the known interactions of ICOS-L with the CD28, CTLA-4 and ICOS immune receptors, the screen was expanded to include B7-1 and B7-2 (the ligands of CD28 and CTLA-4) as query molecules. These efforts identified ISLR2 as a novel B7-1 interacting protein and confirmed the previously reported B7-1:NGFR interaction (FIG. 1C). Importantly, most of the molecules identified in these new interactions possess additional previously defined interacting proteins, resulting in an unanticipated network of interactions revealing previously unappreciated linkages between immune regulatory and neural development/function pathways (Table 1).

Figures 2A, 2B, 2C:
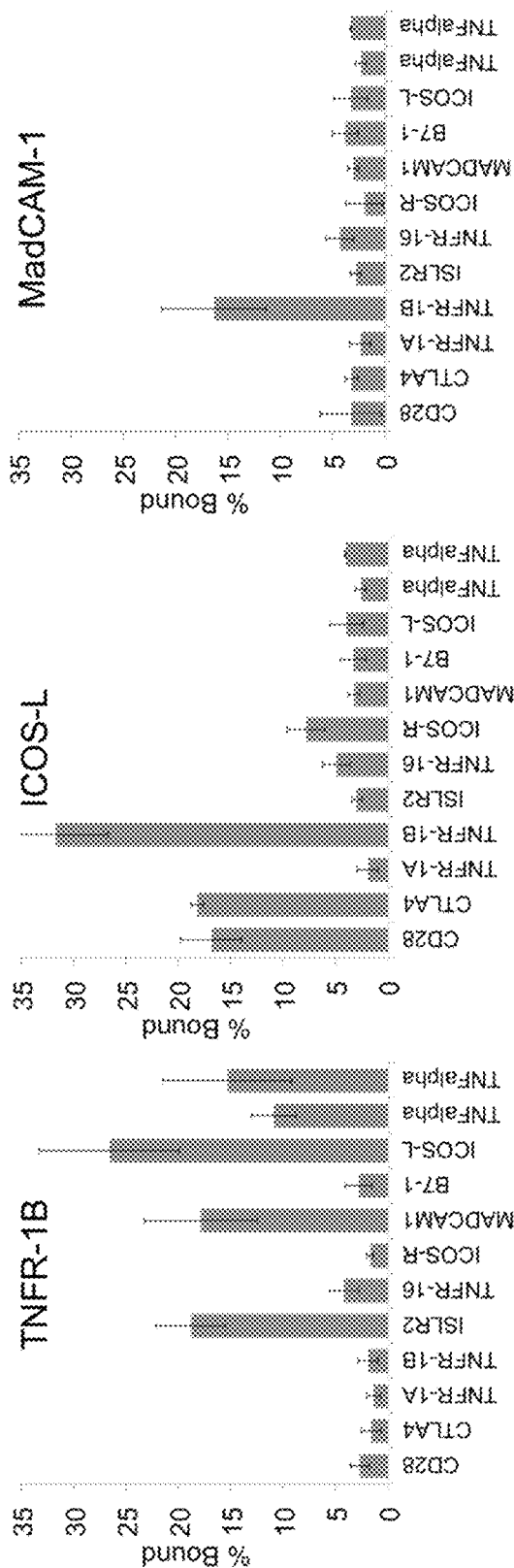
FIG. 2A. Validation of TNFR-1B interactions using full-length genes containing bona fide native transmembrane and cytoplasmic domains. A panel of genes expressed as GFP fusions in HEK 293 cells were challenged with full-length native gene-mCherry fusions of TNFR-1B query. Cell-cell complexes were analyzed by FACS to determine the percent bound calculated as the number of GFP & mCherry double positive events divided by the total number of cell events. Data shows the average percent bound for three independent experiments.
FIG. 2B. Validation of TNFR-1B interactions using full-length genes containing bona fide native transmembrane and cytoplasmic domains. A panel of genes expressed as GFP fusions in HEK 293 cells were challenged with full-length native gene-mCherry fusions of ICOS-L query. Cell-cell complexes were analyzed by FACS to determine the percent bound calculated as the number of GFP & mCherry double positive events divided by the total number of cell events. Data shows the average percent bound for three independent experiments.
FIG. 2C. Validation of TNFR-1B interactions using full-length genes containing bona fide native transmembrane and cytoplasmic domains. A panel of genes expressed as GFP fusions in HEK 293 cells were challenged with full-length native gene-mCherry fusions of MadCAM-1 query. Cell-cell complexes were analyzed by FACS to determine the percent bound calculated as the number of GFP & mCherry double positive events divided by the total number of cell events. Data shows the average percent bound for three independent experiments.
Figure 3:
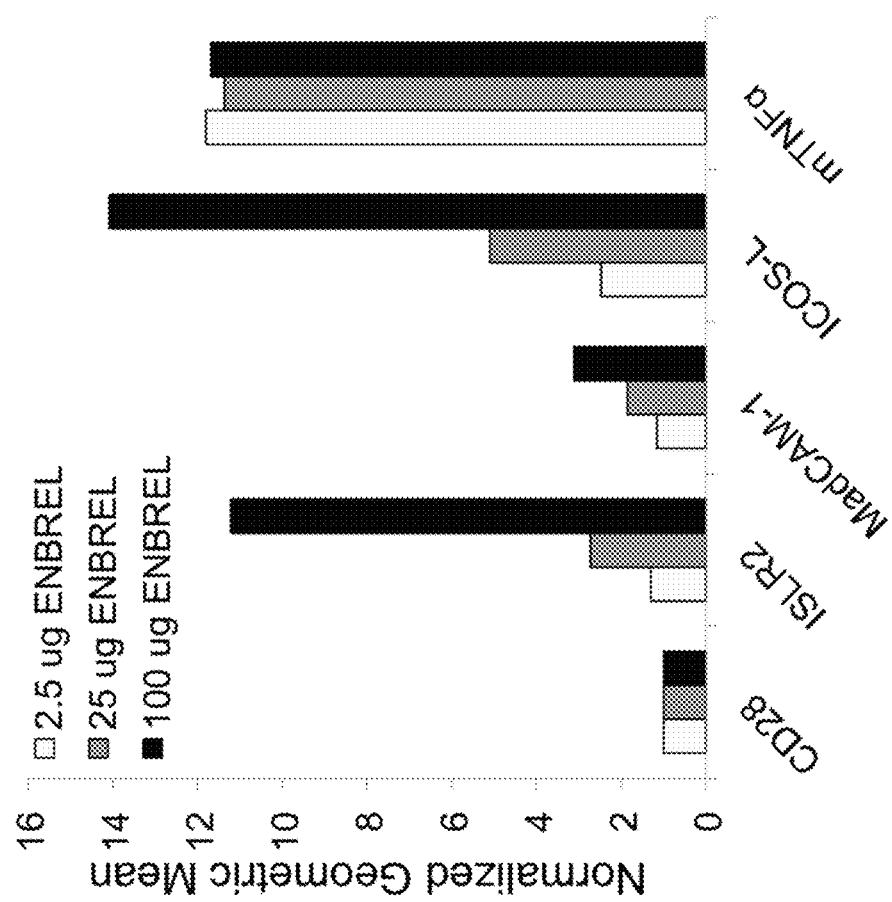
FIG. 3. ENBREL® (etanercept) protein binds to cells expressing TNF-alpha, ICOS-L, MadCAM-1 and ISLR2. ENBREL® (etanercept) protein was used to challenge cells expressing GFP fusions of CD28 (−control), TNF-alpha (+control), ICOS-L, MadCAM-1 or ISLR2. Bound ENBREL® (etanercept) was detected using a goat anti-human Alexa 594-labeled secondary antibody and samples were analyzed by flow cytometry. Data shows the geometric mean of FL4 (Alexa 594) for all live GFP positive cells. At low ENBREL® (etanercept) concentrations (2.5 ug≈100 nM) binding was observed to TNF-alpha and ICOS-L, while binding was observed to MadCAM-1 and ISLR2 at higher ENBREL® (etanercept) concentrations (25 ug and 100 ug).

Further validation studies were performed for the TNFR-1B interactions. Cell-cell FACS assays using cells expressing full-length native versions (i.e., containing native transmembrane and cytoplasmic segments) of TNFR-1B, ICOS-L and MadCAM-1 were fully consistent with the original screen (FIG. 2). Furthermore, soluble ENBREL® (etanercept) protein binds to cells expressing all three of these novel ligands, as well as its well-characterized ligand TNF-alpha when expressed on cells (FIG. 3). Additionally, a soluble Fc-fusion construct of ICOS-L exhibited binding to cells expressing TNFR-1B, providing further validation of this interaction. These results indicate that the mechanism of ENBREL® (etanercept) is more complex than currently appreciated (i.e., TNF-alpha sequestration is not the sole contributing factor to the therapeutic function of ENBREL®

(etanercept)) and provide the foundation for the generation of ENBREL® (etanercept) variants possessing modified affinities and selectivities with enhanced therapeutic potential and reduced side effects (e.g., the generation of TNFR-1B variants that solely recognize TNF-alpha, or mutants that recognize only one of the identified TNFR-1B-binding proteins (ICOS-L, MadCAM-1 or ISLR2) or mutants that exhibit increased affinities for some or all TNFR-1B-binding proteins, or mutants that exhibit reduced affinities for some ligands compared to TNFR-1B and enhanced affinities for some ligands compared to TNFR-1B).

Figures 4A, 4B, 4C:
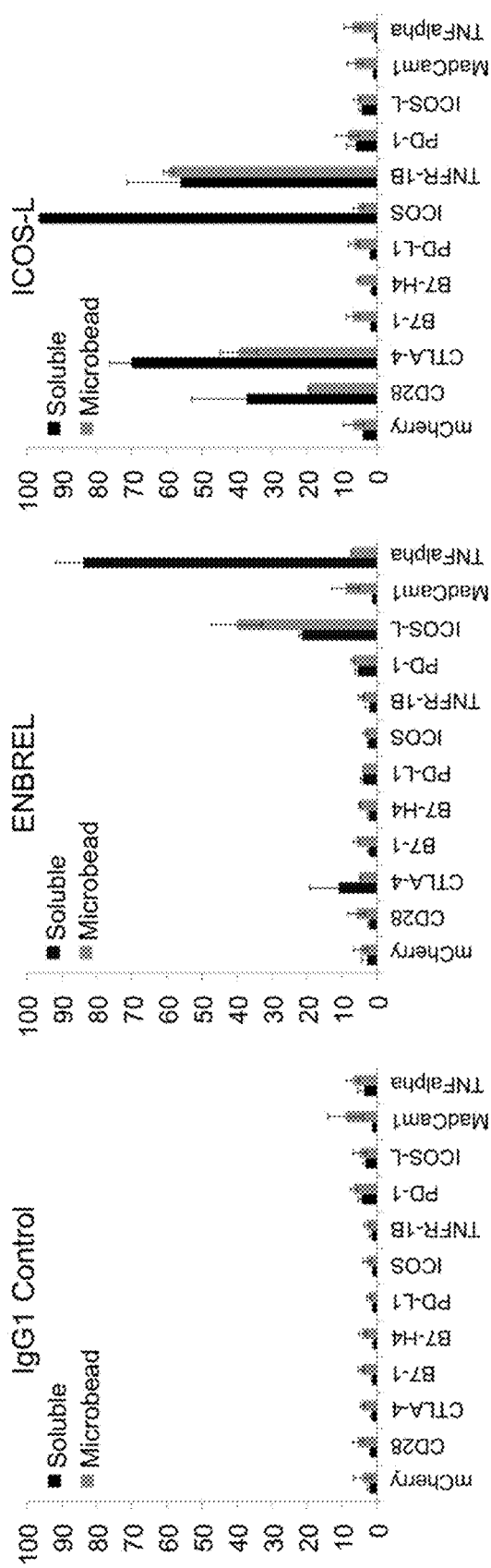
FIG. 4A-4E. Validation of ENBREL® (etanercept) and ICOS-L binding using a two different protein binding assays. A)-C) A panel of 12 different mCherry constructs were transiently transfected into HEK 293 cells. A)—IgG1 Control, B)—ENBREL® (etanercept), C)—ICOS-L. Three days post transfection cells were challenged in parallel with either soluble Fc-fusion protein or microbeads coated with the same protein. The ICOS-L Fc (IgG2a) and control protein were expressed in HEK 293 cells using transient transfection and subsequently purified by Ni2+-NTA and gel filtration chromatography. Anti-human-IgG Alexa-Fc 488 secondary antibody was used to detect soluble protein and microbeads were spiked with FITC Fc to label them green. Data show the percent of mCherry positive HEK cells bound to either protein or microbeads and are the average of two independent experiments. D) FACS scatter plots showing mCherry signal (y-axis) and Alexa 488 signal (x-axis) from one replicate of the soluble protein binding experiment (i.e. data in A represents two independent experiments). E) Same as in B but showing data from one replicate of the microbead binding experiment.
Figure 4D:
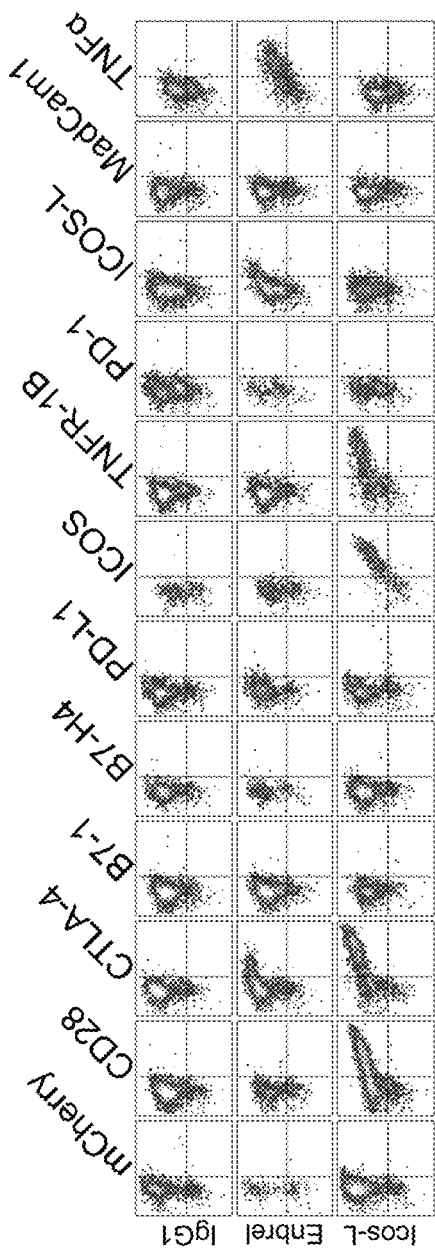
Figure 4E:
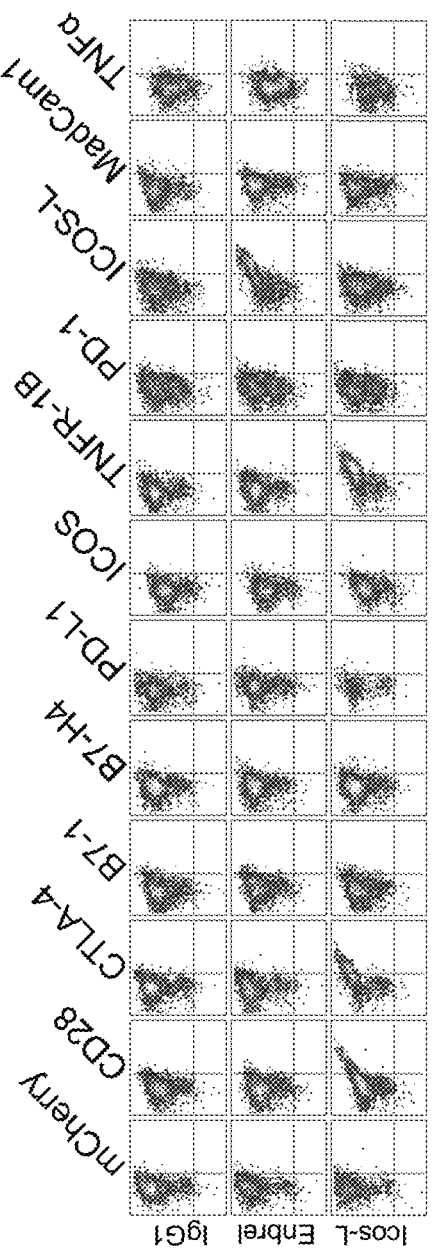

Using a high-throughput cell-cell screen, ICOS-L, MadCAM-1 and ISLR2 were identified as three novel ligands of TNFR-1B. To further evaluate these interactions, two different in vitro assays that utilize purified protein reagents were used. The first was a soluble protein-binding assay in which Fc-fusion protein (IgG1 control, ENBREL® (etanercept, a IgG1 fusion of TNFR-1B) or ICOS-L IgG1) was added directly to HEK 293 cells expressing a panel of cell surface receptors (FIG. 4A-4D). The second was a microbead-binding assay in which the same Fc-fusion proteins were used to coat protein-A microspheres that were subsequently added to HEK 293 cells expressing the same panel of cell surface receptors (FIG. 4A-4C and 4E). Soluble binding of ENBREL® (etanercept) was observed to cell surface expressed TNFα and to the newly identified target ICOS-L. Interestingly, when presented on microbeads, ENBREL® (etanercept) failed to bind to TNFα but showed improved binding to ICOS-L (compared to soluble protein). These data suggest that by modulating the valency of ENBREL® (etanercept), a therapeutic derivative could be designed that affords enhanced recognition of ICOS-L. Binding was observed of soluble ENBREL® (etanercept) to cells expressing MadCAM-1 and ISLR2 but only at a high concentration of ENBREL® (etanercept) (100 µg) (FIG. 3). This suggests these interactions are either lower affinity or require a specific orientation that is only available in the context of cell surface expression. Indeed at lower ENBREL® (etanercept) concentrations (0.5-2.5 µg), binding was only observed to cells expressing ICOS-L and TNFα but not to cells expressing MadCAM-1 and increasing the avidity using microbeads did not rescue MadCAM-1 binding (FIGS. 3 and 4). Soluble ICOS-L Fc-fusion protein bound to cells expressing all three of its previously reported receptors (CD28, CTLA-4 and ICOS), as well as to cells expressing TNFR-1B, further validating this interaction (FIGS. 3 and 4). Unexpectedly, microbead-bound ICOS-L did not exhibit binding to cells expressing ICOS, and showed reduced binding to cells expressing CD28 and CTLA-4, but maintained binding to cells expressing TNFR-1B. This behavior indicates that these interactions are sensitive to specific orientations and overall organizations, and support the design of deliberately engineered mutants with modified selectivity; i.e., reduced or enhanced affinities for all binding partners or a subset of binding partners. This is demonstrated immediately below.

Figure 5A:
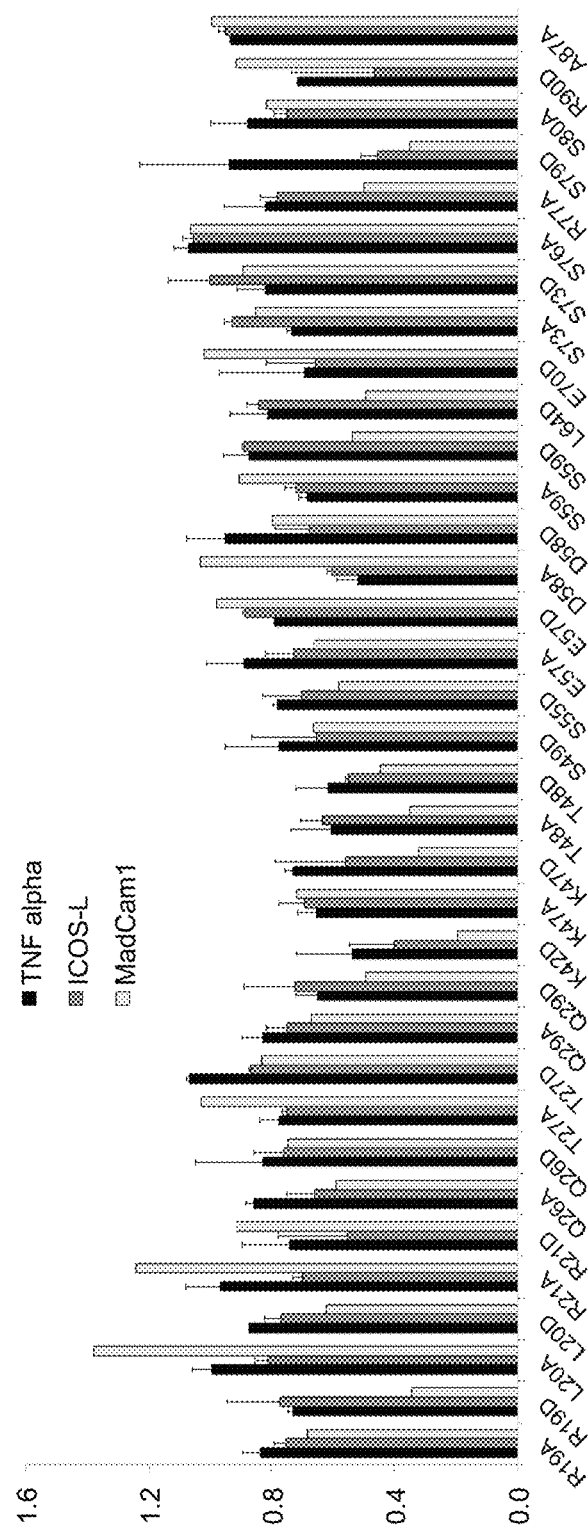
FIG. 5A-5F. Identification of TNFR-1B mutants with modulated affinities and selectivties for ligands. A)-B) A panel of TNFR-1B mutants was generated by site-directed mutagenesis of surface accessible positions within the ectodomain of TNFR-1B. The TNFR-1B mutants were transiently expressed as mCherry fusions in HEK 293 and subsequently challenged with cells expressing GFP fusions of cell-surface displayed TNFα, ICOS-L or MadCAM-1. Data show the bound events as a fraction of all mCherry positive cells (mutant expression) and are the average of two independent experiments. C) The crystal structure of the TNFR-1B/TNFα complex (PDB: 3ALQ) highlighting residues of interest identified in the mutant screen that effect binding of three TNFR-1B ligands (TNFα, ICOS-L and MadCAM-1). For comparison, the chart shows the average fraction bound (from the screen) for the mutants identified. D) The same as in C highlighting TNFR-1B mutants that effect binding of ICOS-L and MadCam-1 but not TNFα. E) The same as in C highlighting mutations that effect MadCAM1 binding only. F) The same as in C showing one mutant that effected TNFα and ICOS-L but not MadCAM1.
Figure 5B:
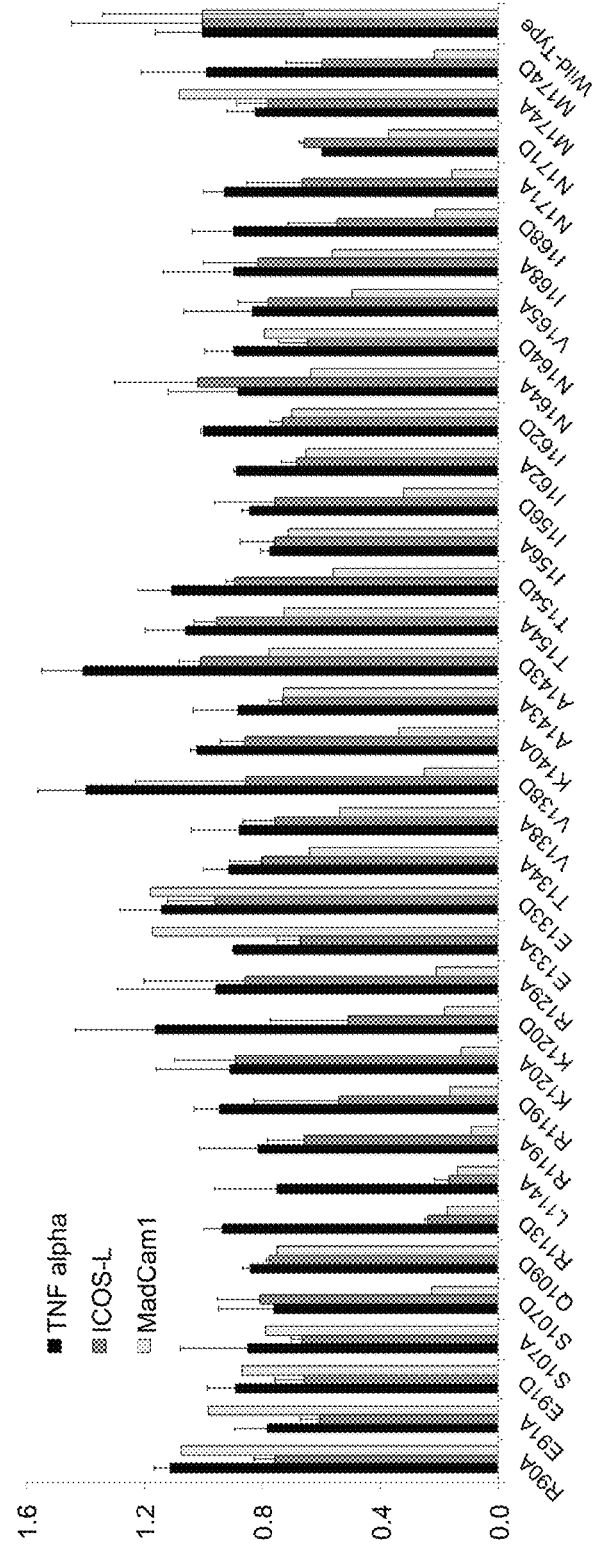
Figure 5C:
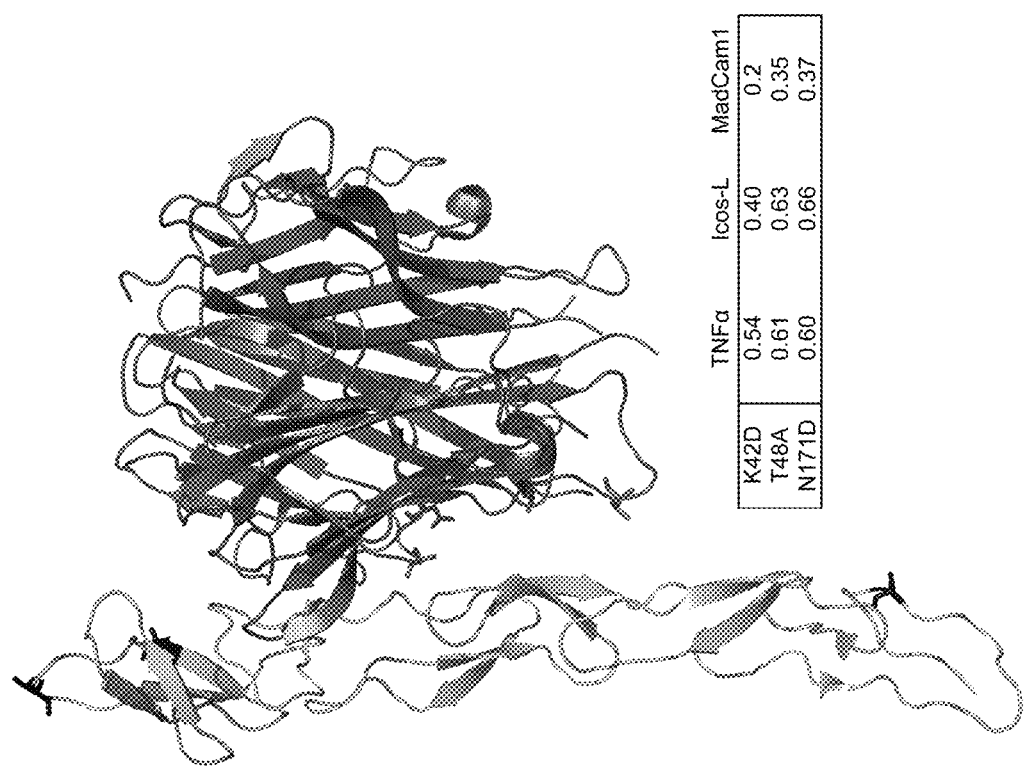
Figure 5D:
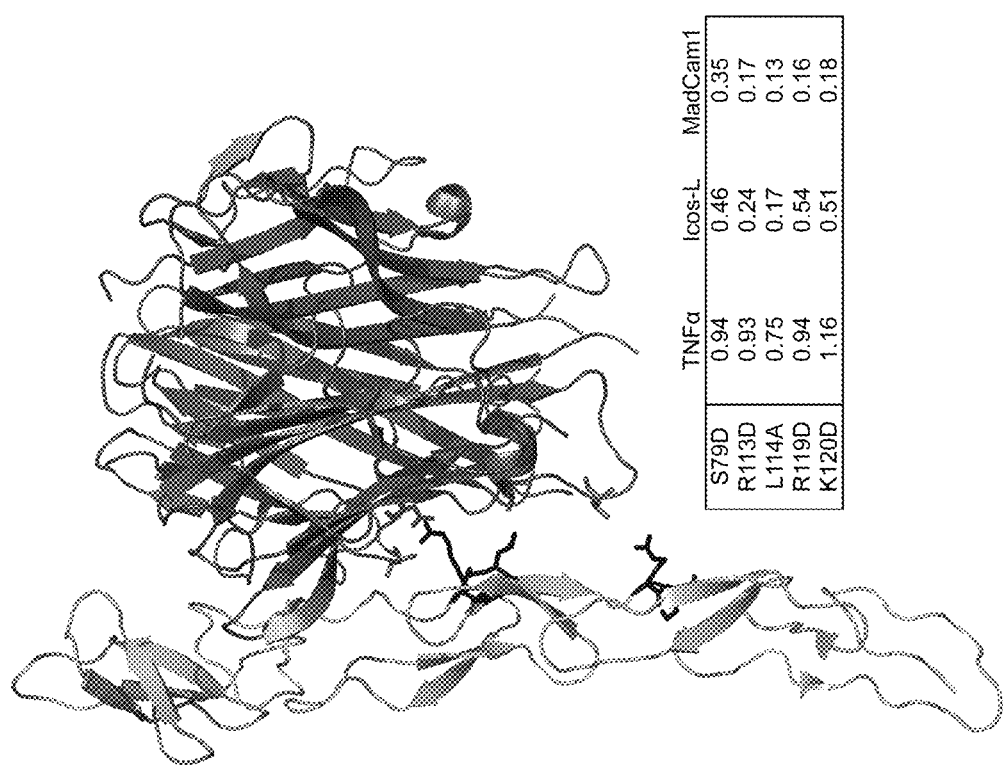
Figure 5E:
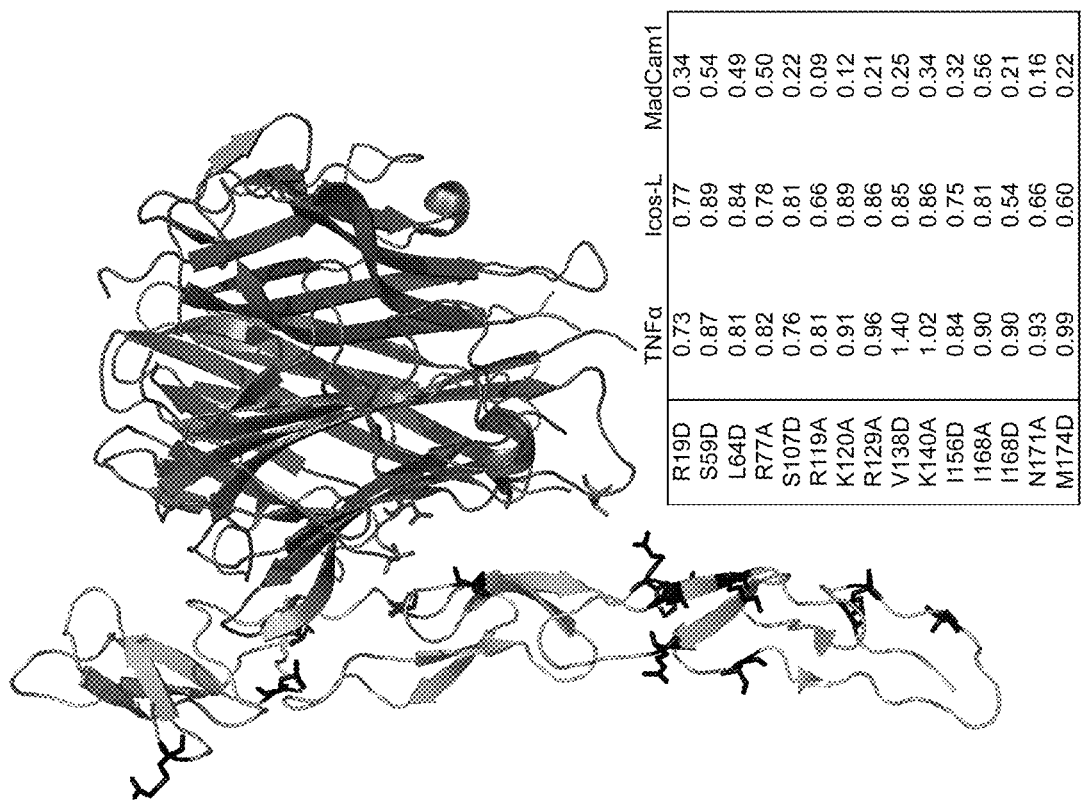
Figure 5F:
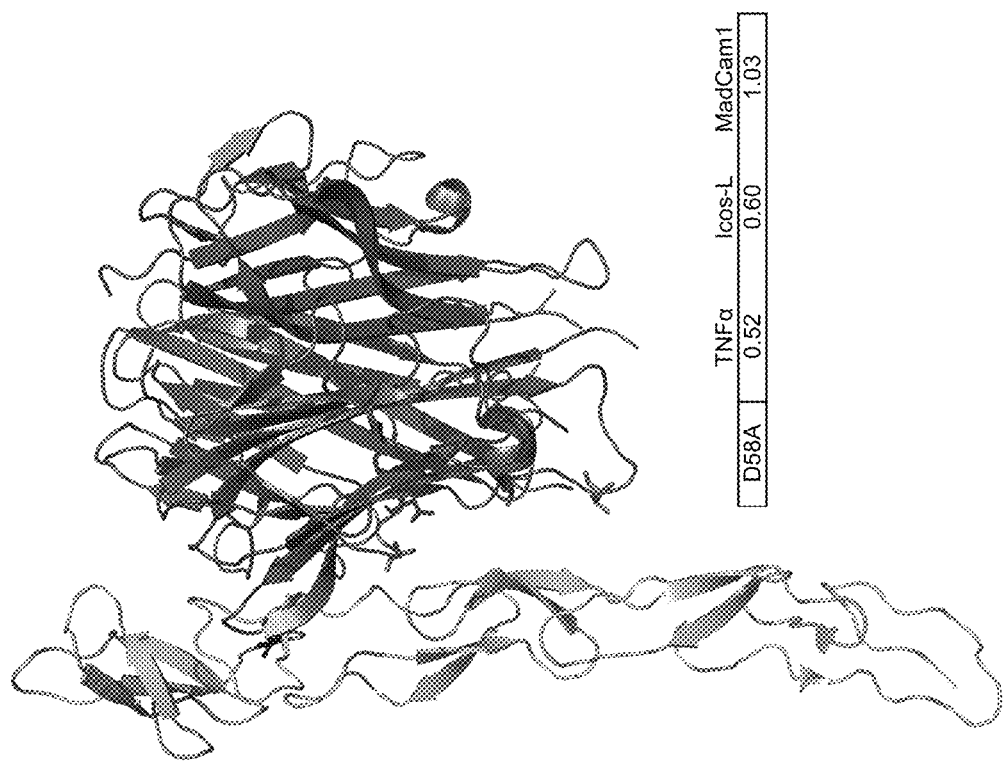

It was also examined whether specific mutants of TNFR-1B could be identified that exhibited selective, enhanced and/or reduced recognition of its multiple ligands. A panel of 71 TNFR-1B point mutants was generated and screened for binding to TNFα, ICOS-L and MadCAM-1 using the cell-cell FACS assay (FIG. 5A-5B). Three mutants (K42D, T48A and N171D) were identified that modulated binding to all three ligands (FIG. 5C); binding to TNFα and ICOS-L was reduced to ~50% of wild-type, while binding to MadCAM-1 was more significantly reduced. One mutant, D58A, showed reduced binding to TNFα and ICOS-L but not MadCAM-1 (FIG. 5F). However, five mutants (S79D, R113D, L114A, R119D, K120D) were identified that greatly reduced binding of TNFR-1B to ICOS-L and MadCAM-1, but which did not significantly modify recognition of TNFα (FIG. 5D). Two of the mutants R113D and L114A showed almost no binding to ICOS-L and MadCAM-1, while retaining near wild-type binding to TNFα. In addition, mutants were identified that predominately affected binding of MadCAM-1 (R19D, S59D, L64D, R77A, S107D, R119A, K120A, R129A, V138D, K140A, I156D, I168D, N171A, M174D) (FIG. 5E). This set of mutants, extending over much of the length of TNFR-1B, suggests that the MadCAM-1 recognition surface on TNFR-1B is more extensive than the recognition surfaces for ICOS-L and TNFα.

These data suggest that the binding sites for ICOS-L and MadCAM-1 on TNFR-1B overlap, at least in part, that of TNFα. They also demonstrate the feasibility of generating TNFR-1B variants with engineered properties/selectivities (e.g., high selectivity for only TNFα, or other subsets of ligands with increased or decreased affinities).

Figure 6A:
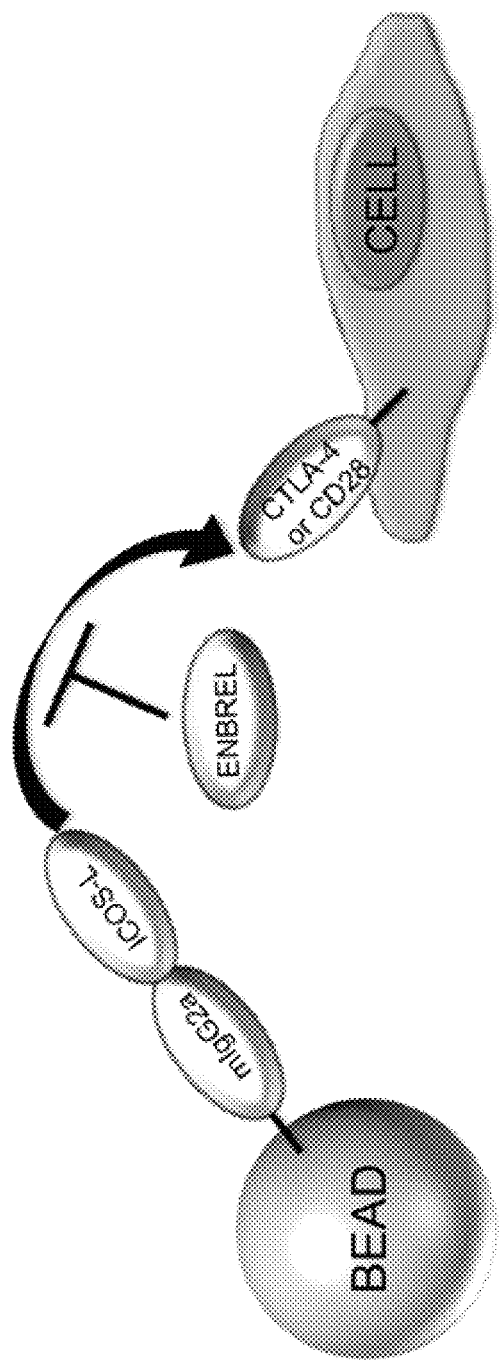
FIG. 6A-6C. ENBREL® (etanercept) competes with cell surface expressed CTLA-4 and CD28 for ICOS-L binding. A) Schematic of competition assay setup. B)-C) Cells expressing either CTLA-4 (B) or CD28 (C) as a C-terminal mCherry fusion protein were challenged with green fluorescent protein A microbeads coated with purified hICOS-L, B7-1 or B7-2 protein in the absence or presence of increasing ENBREL® (etanercept) concentration. Flow cytometry analysis was used to determine the percentage of mCherry positive cells bound to microbeads. Data were normalized to % bound in the absence of ENBREL® (etanercept) and represent the average and standard deviation from two independent experiments.
Figures 6B, 6C:
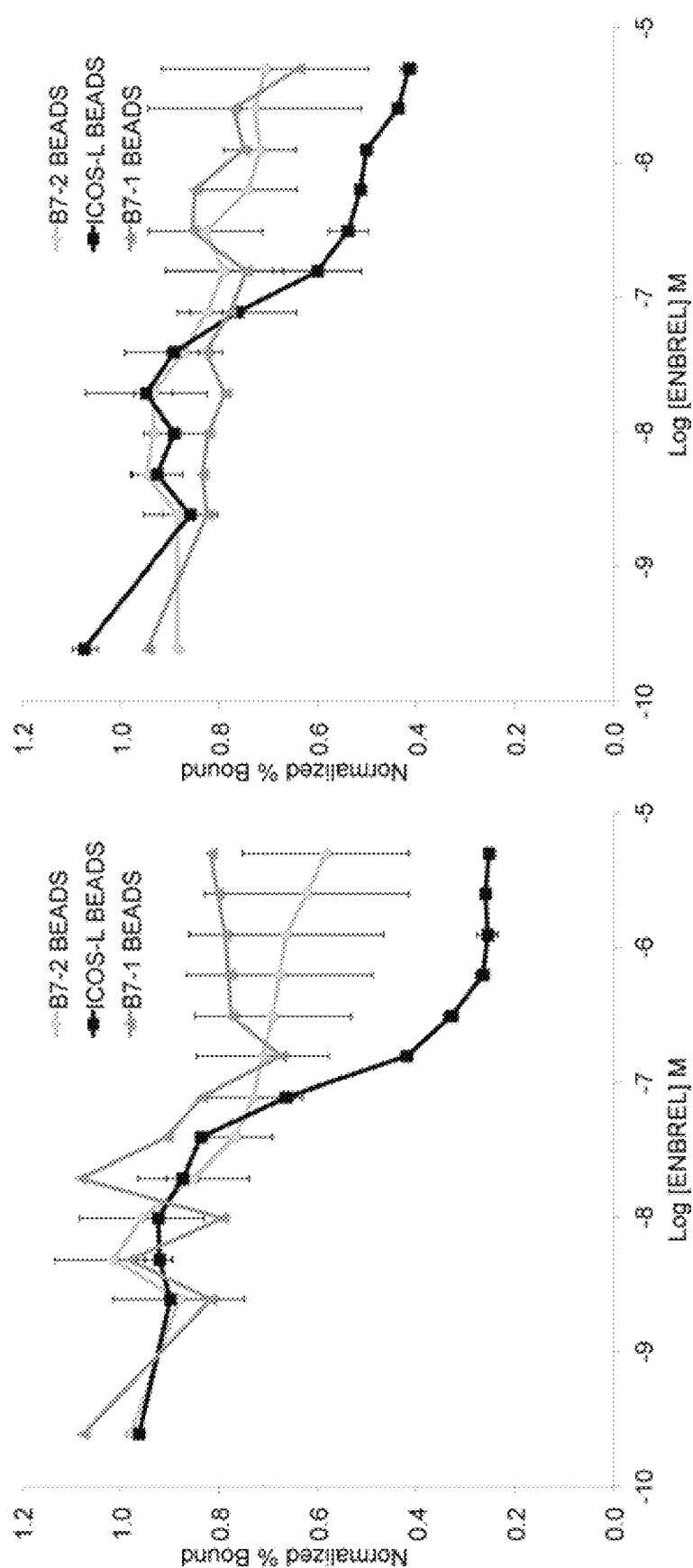

A cell based competition binding experiment was used to determine whether ENBREL® (etanercept) could block ICOS-L interactions with CTLA-4 and CD28 (FIG. 6). In this experiment cells expressing either CTLA-4 or CD28 were expressed on the cell surface and subsequently queried with ICOS-L, B7-1 or B7-2 presented on the surface of a bead in the absence or presence of soluble ENBREL® (etanercept). The data show ENBREL® (etanercept) more significantly blocked binding of ICOS-L coated beads to both CTLA-4 and CD28 expressing cells compared to B7-1 or B7-2 coated beads. This result suggests that ENBREL® (etanercept) has the ability to act as a specific competitor with CD28 and CTLA-4 and perhaps ICOS for binding to ICOS-L and thus disrupting endogenous ICOS-L mediated signaling in vivo. A separate bead-based in vitro competition experiment was used to test whether TNFα could compete with ICOS-L for binding to ENBREL® (etanercept). The data show that protein A beads coated with ENBREL® bind to soluble ICOS-L, which can then be competed off by the addition of TNFα. This suggests the binding site for ICOS-L on TNFR-1B overlaps that of TNFα and supports previously described TNFR-1B binding interface mapping data. Thus, not only may ENBREL® (etanercept) be disrupting endogenous ICOS-L activity but ICOS-L could interfere with the ability of ENBREL® (etanercept) to efficiently modulate TNFα.

Figure 7A:
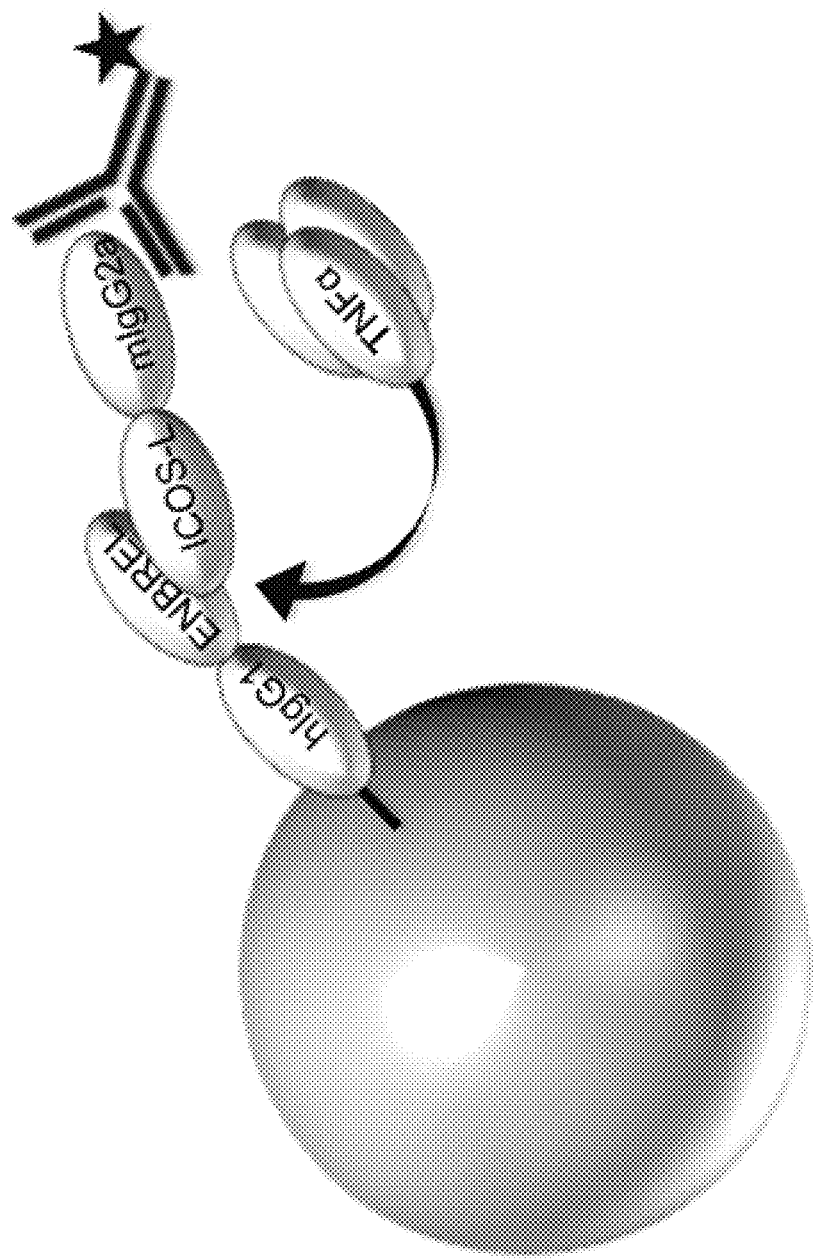
FIG. 7A-7B. TNFα competes with ICOS-L for binding to ENBREL® (etanercept). A) Schematic of competition assay setup. B) Inset: Protein A beads were coated with ENBREL® (etanercept) or control hIgG1 protein and incubated with increasing concentrations of ICOS-L mIgG2a protein. Binding of ICOS-L to beads was detected using a goat anti-mouse Alexa 488 secondary antibody and the percent of beads bound was quantified by flow cytometry. For the competition experiment, ENBREL® (etanercept) coated protein A beads were pre-incubated with 10 nM ICOS-L mIgG2a (saturating) and subsequently incubated with increasing concentrations of TNFα. Flow cytometry analysis was used to determine the extent of TNFα dependent loss of ICOS-L binding. Data show the geometric mean for the 488 Alexa channel (ICOS-L binding) for all beads and represent the average and standard deviation from two independent experiments.
Figure 7B:
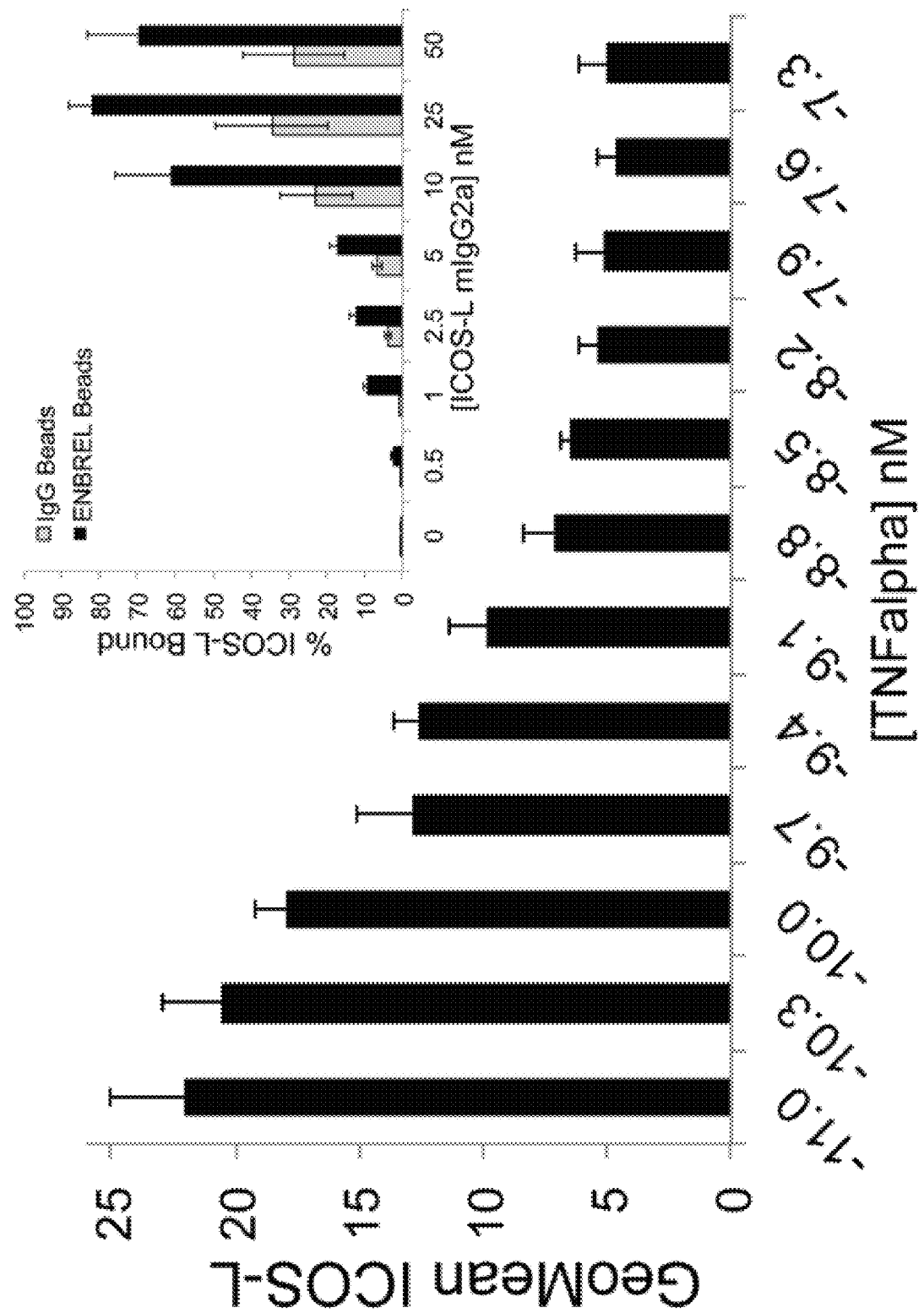
Figure 8:
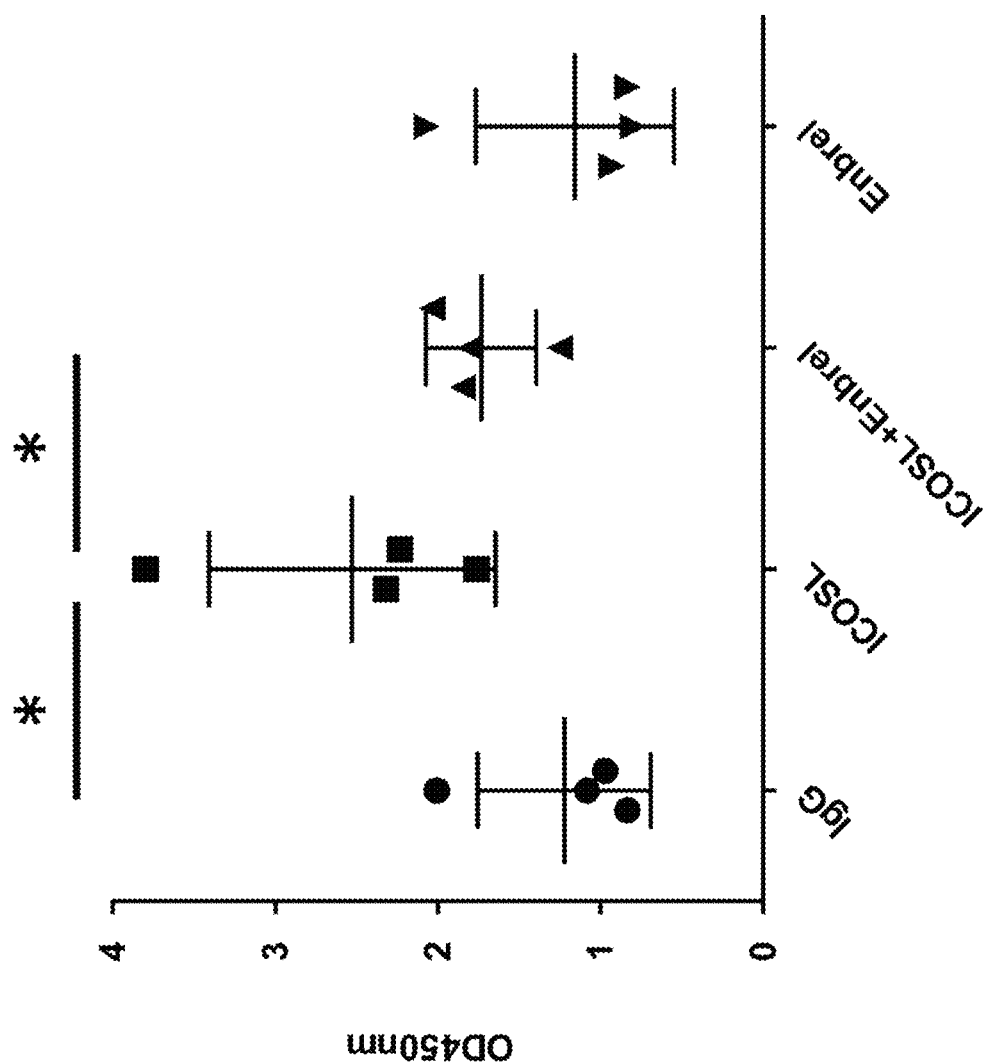
FIG. 8. ENBREL® (etanercept) reduces ICOS-L mediated co-activation in primary human T-cells. T-cells were purified from PBMC (peripheral blood mononuclear cells) from 4 individual donors. $2 \times 10^5$ T-cells were activated with 2.5 µg/ml anti-CD3 and 1 µg/ml anti-CD28 in the presence of control Ig (1 µg/ml), ICOS-L-Ig (1 µg /ml), ENBREL® (etanercept) (20 µg/ml) & ICOS-L-Ig (1 µg/ml) or ENBREL® (etanercept) alone (20 µg/ml). Three days post-activation proliferation was measured using a cell counting kit (CCK-SK).
Figures 9A, 9B:
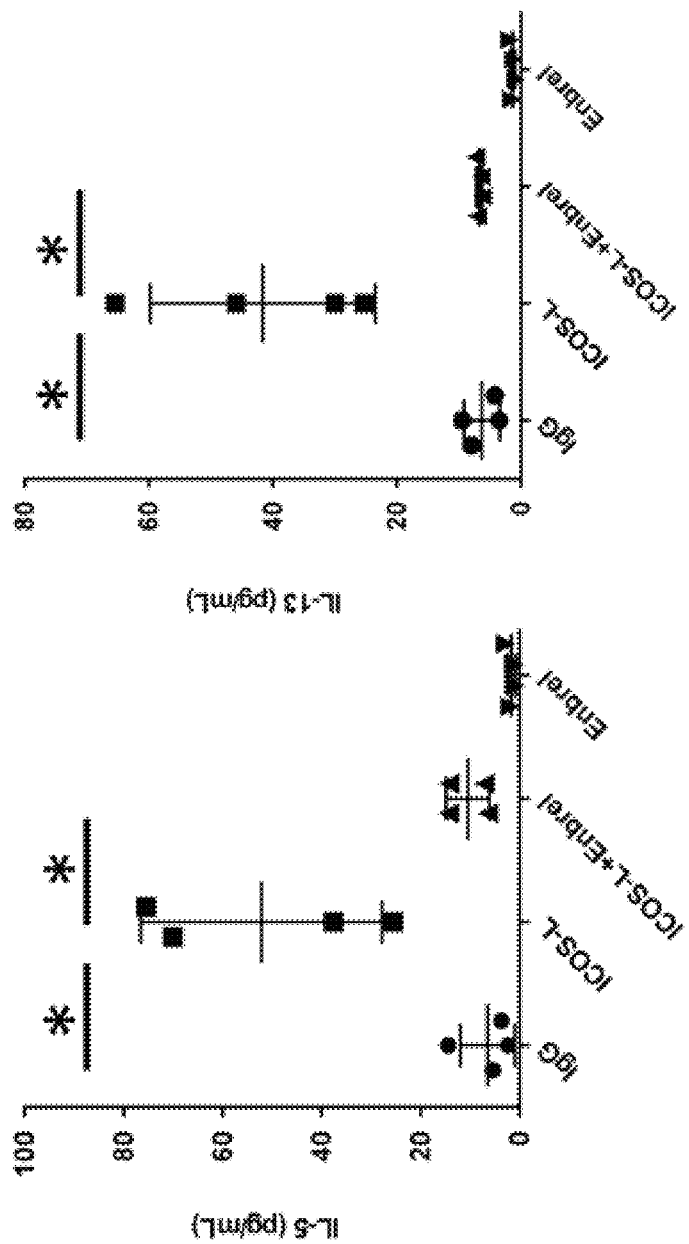
FIG. 9A-9E. ENBREL® (etanercept) reduces ICOS-L mediated cytokine release from primary human T-cells. Cytokine production (A)—IL-5, B)—IL-13, C)—IL-4, D)—IL-21, E)—IFN-gamma) from 4 primary human T-cell populations was quantified three days post-activation in the presence of control Ig (1 µg/ml), ICOS-L-Ig (1 µg/ml), ENBREL® (etanercept) (20 µg/ml) & ICOS-L-Ig (1 µg/ml) or ENBREL® (etanercept) alone (20 µg/ml).
Figures 9C, 9D, 9E:
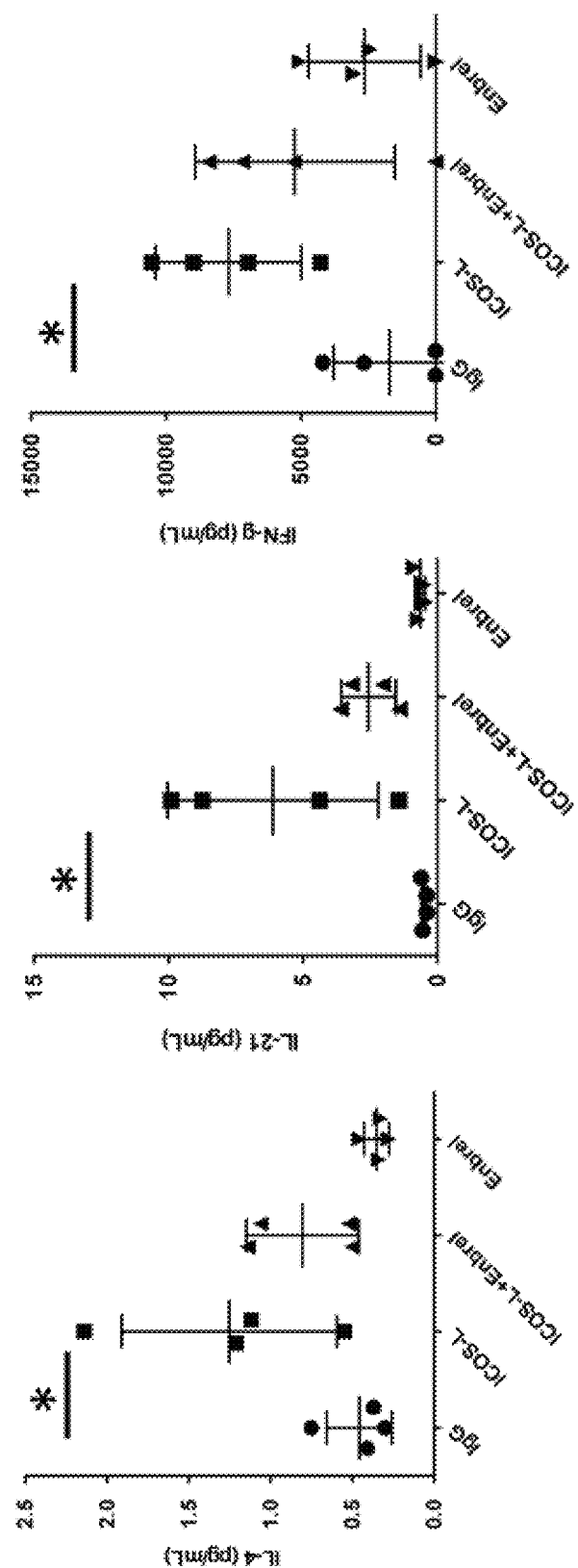
Figure 10:
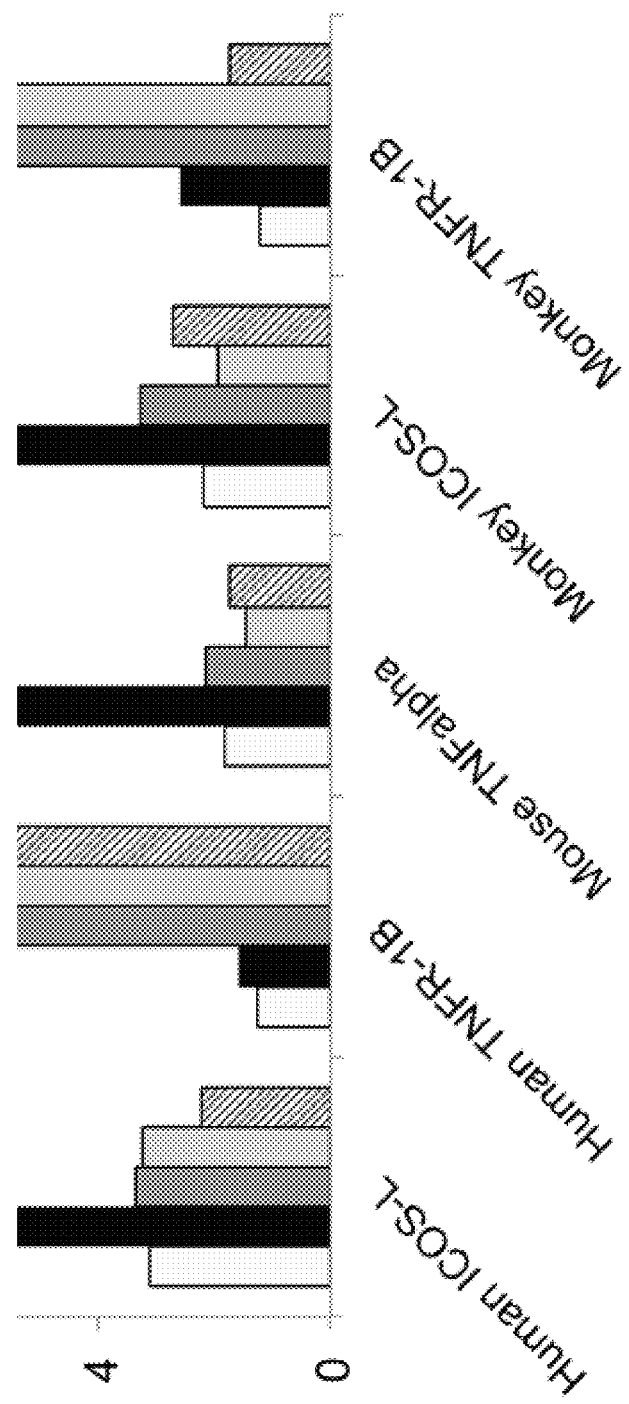
FIG. 10. Cell-cell binding between rhesus monkey (*Macca mulatta*) and human orthologs of TNFR-1B and ICOS-L. HEK 293 cells transiently expressing Cterm GFP fusions of Human ICOS-L, Human TNFR-1B, Mouse TNFalpha, Monkey ICOS-L or Monkey TNFR-1B were challenged with separate HEK 293 cells expressing mCherry fusions of the listed genes. The extent of cell-cell binding was determined by flow cytometry and the % bound calculated as the percent of all double positive events.

In a subsequent experiment, human peripheral T-cells were isolated from four individual donors and used in in vitro T-cell activation experiments (FIGS. 8 and 9). ICOS-L can induce a co-activation signal in human T-cells above that of the initial stimulatory signals that occur upon TCR and CD28 engagement. This enhancement of T-cell activation resulted in increased production of several cytokines including, IL-5, IL-13, IL-4, IL-21 and IFN-gamma and TNF-alpha. Therefore it was tested whether ENBREL® (etanercept) could block this ICOS-L dependent co-activating signal (FIG. 7). The data show that ENBREL® (etanercept) significantly inhibited ICOS-L dependent T-cell activation (as measured by cell proliferation) whereas ENBREL® (etanercept) alone had no effect on T-cell proliferation. In addition, ENBREL® (etanercept) resulted in a reduction in the level of those cytokines produced by ICOS-L mediated T-cell coactivation, most significantly in IL-5 and IL-13 levels (FIG. 8). Interestingly, both IL-5 and IL-13 are predominately involved in B-cell activation and function and are implicated in asthma and other allergic respiratory illnesses. The use of anti-TNFalpha therapeutics in the treatment of asthma have yielded mixed results in a 2005 study, treatment of patients with severe asthma patients with ENBREL® (etanercept) resulted in improvements of asthma symptoms; however; more recent studies have shown any impact of ENBREL® (etanercept) treatment to be highly variable.

With the goal of generating a mouse model to examine the ICOS-L: TNFR-1B dependent effects in vivo, mouse constructs of both TNFR-1B and ICOS-L were tested. Unfortunately the mouse orthologs of ICOS-L and TNFR-1B do not bind to one another nor does ENBREL® (etanercept) bind to mouse ICOS-L (data not shown). The mouse versus human percent identify for ICOS-L and TNFR-1B are 45% and 63%, respectively, so it is perhaps not surprising that the binding phenotype is different. Orthologs of ICOS-L and TNFR-1B were next examined from rhesus monkey (*Macca mulatta*), which shares 91% and 96% homology with human, respectively. Binding was examined in the cell-cell FACS binding assay and significant binding observed between monkey ICOS-L and mTNFR-1B as well as the monkey proteins and their human counterparts, indicating a usefulness of monkey models of autoimmune disease.

DISCUSSION

ICOS-L is the ligand for the inducible costimulatory molecule (ICOS), which controls a major T cell costimulatory pathway that represents a significant therapeutic target. ICOS-L is a major immune regulatory ligand expressed on monocytes, dendritic cells, and B cells, as well as other antigen presenting cells. Expression of ICOS-L on B-cells plays a significant role in the production of antibodies within the germinal center and is necessary for the development of rheumatoid arthritis [2, 3]. Expression of ICOS-L in dendritic cells has been increasingly associated with Crohn's disease and ulcerative colitis [4, 5]. Interestingly, in a subset of cell types (B-cells, monocytes, lung epithelial cells), TNF-alpha induces ICOS-L expression via activation of the NFKappaB pathway [6]. The present data demonstrating a direct interaction between ICOS-L and TNFR-1B suggests the presence of additional cross talk between the ICOS-L/ICOS and TNF-alpha/TNFR-1B pathways, which potentially impacts both therapeutic mechanisms and treatment strategies.

MadCAM-1, mucosal vascular addressin cell adhesion molecule 1, also known as addressin, is an endothelial cell adhesion molecule from the Ig superfamily that interacts preferentially with the leukocyte beta7 integrin LPAM-1 (alpha4/beta7), L-selectin, and VLA-4 (alpha4/beta1) on myeloid cells to direct leukocytes into mucosal and inflamed tissues [7]. MadCAM-1 expression is elevated in the intestinal tissue of both Crohn's disease and ulcerative colitis patients, but was more abundant and appeared in deeper tissues in patients with Crohn's disease [7]. The present results are the first indication of an association between MadCAM-1 and TNFR-1B. Notably, the ICOS-L [8-10] and MadCAM-1 [11] pathways are both themselves active targets for immunotherapy.

ISLR-2 (Immunoglobulin superfamily containing leucine-rich repeat protein 2) is believed to interact with TrkA and Ret receptor tyrosine kinases to regulate axonal extension, guidance and branching during neural development [13].

These interactions are of considerable clinical importance as soluble TNFR-1B is marketed as ENBREL® (etanercept), a leading treatment for rheumatoid arthritis, psoriatic arthritis, ankylosing spondylitis, and plaque psoriasis in adults, as well as juvenile idiopathic arthritis in children. The mechanism of action of ENBREL® (etanercept) is thought to be the targeting and binding of TNF, which results in the blockade of the TNF-mediated signaling pathways and an associated global inhibition of immune responsiveness [14, 15]. The identification of these additional "off-target" interactions for TNFR-1B may provide new insights into the mechanisms of ENBREL® (etanercept) function, including its range of effective clinical indications and its considerable deleterious side effects, and offer the opportunity to develop "second generation ENBREL®s" with enhanced potency and reduced side effects. Furthermore, the involvement of both ICOS-L and MadCAM-1 in the onset of Crohn's disease, inflammatory bowel disease and ulcerative colitis suggests that development of new "ENBREL®" proteins with altered activity for one or both of these targets might create a therapeutic agent better suited to treat these diseases than the currently marketed ENBREL® (etanercept), which has been proven less effective in their treatment of these particular diseases [12].

The present study identified new TNFR-1B interactors and demonstrated that TNFR-1B is a naturally occurring multi-specific receptor. This multi-specificity offers new opportunities for therapy (based, e.g., on the functional significance of interactions between TNFR-1B and TNFα, ICOS-L or MadCAM-1). The present approach provides the identification of new networks of interactions that impact this biology. These findings enable generation of TNFR-1B variants with novel properties and selectivities. This includes, but is not limited to, TNFR-1B variants which only recognize one ligand (e.g., TNFa, or MadCAM-1, or ICOS-L, or ISLR2), or with enhanced affinities for all ligands, or with reduced affinities for all ligands, or with enhanced affinities for some ligands (e.g., to provide more effective multi-specific reagents), or with reduced affinities for some ligands (e.g., to provide more effective multi-specific reagents). These variants can be identified by large-scale mutagenesis. Using single point mutants, it was demonstrated that considerable modulation of selectivity can be achieved (FIG. 5). Additional properties can be realized by incorporation of multiple point mutants and by a variety of selection strategies. Variants generated by manipulating valency can afford enhanced selectivity/avidity. This is based on the comparison of cell-cell vs microbead-cell data in FIG. 4. These altered biochemical properties can be translated into new therapeutic strategies and opportunities.

TABLE 1

Signaling networks defined by this disclosure.

| Newly Discovered in this Disclosure | Previously Reported interactions |
| --- | --- |
| TNFR-1B:ICOS-L | TNFR-1B:TNF-α |
|  | ICOS-L:CD28; ICOS-L:CTLA-4; |
|  | ICOS-L:ICOS |
| TNFR-1B:MadCAM-1 | MadCAM-1:LPAM-1integrin; |
|  | MadCAM-1:L-selectin; MadCAM-1:VLA-4 |
| TNFR-1B:ISLR2 | ISLR2:TrkA RTK; ISLR2:Ret RTK |
| B7-1:ISLR2 | B7-1:CTLA-4; B7-1:CD28; B7-1:PD-L1; |
|  | B7-1:NGFR |

REFERENCES

1. Yao S, Zhu Y, Zhu G, Augustine M, Zheng L, Goode D J, Broadwater M, Ruff W, Flies S, Xu H et al: B7-h2 is a costimulatory ligand for CD28 in human. *Immunity* 2011, 34(5):729-740.

2. Liu D, Xu H, Shih C, Wan Z, Ma X, Ma W, Luo D, Qi H: T-B-cell entanglement and ICOSL-driven feed-forward regulation of germinal centre reaction. *Nature* 2015, 517 (7533):214-218.
3. Hamel K M, Cao Y, Olalekan S A, Finnegan A: B cell-specific expression of inducible costimulator ligand is necessary for the induction of arthritis in mice. *Arthritis & rheumatology* 2014, 66(1):60-67.
4. Xin L, Jiang T T, Chaturvedi V, Kinder J M, Ertelt J M, Rowe J H, Steinbrecher K A, Way S S: Commensal microbes drive intestinal inflammation by IL-17-producing CD4+ T cells through ICOSL and OX40L costimulation in the absence of B7-1 and B7-2. *Proceedings of the National Academy of Sciences of the United States of America* 2014, 111 (29): 10672-10677.
5. Hedl M, Lahiri A, Ning K, Cho J H, Abraham C: Pattern recognition receptor signaling in human dendritic cells is enhanced by ICOS ligand and modulated by the Crohn's disease ICOSLG risk allele. *Immunity* 2014, 40(5):734-746.
6. Richter G, Hayden-Ledbetter M, Irgang M, Ledbetter J A, Westermann J, Korner I, Daemen K, Clark E A, Aicher A, Pezzutto A: Tumor necrosis factor-alpha regulates the expression of inducible costimulator receptor ligand on CD34(+) progenitor cells during differentiation into antigen presenting cells. *The Journal of biological chemistry* 2001, 276(49):45686-45693.
7. Arihiro S, Ohtani H, Suzuki M, Murata M, Ejima C, Oki M, Kinouchi Y, Fukushima K, Sasaki I, Nakamura S et al: Differential expression of mucosal addressin cell adhesion molecule-1 (MadCAM-1) in ulcerative colitis and Crohn's disease. *Pathology international* 2002, 52(5-6): 367-374.
8. Fu T, He Q, Sharma P: The ICOS/ICOSL pathway is required for optimal antitumor responses mediated by anti-CTLA-4 therapy. *Cancer research* 2011, 71(16): 5445-5454.
9. Pan X C, Guo L, Deng Y B, Naruse K, Kimura H, Sugawara Y, Makuuchi M: Further study of anti-ICOS immunotherapy for rat cardiac allograft rejection. *Surgery today* 2008, 38(9):815-825.
10. Nelson M H, Kundimi S, Bowers J S, Rogers C E, Huff L W, Schwartz K M, Thyagarajan K, Little E C, Mehrotra S, Cole D J et al: The Inducible Costimulator Augments Tc17 Cell Responses to Self and Tumor Tissue. *Journal of immunology* 2015.
11. Ueha S, Murai M, Yoneyama H, Kitabatake M, Imai T, Shimaoka T, Yonehara S, Ishikawa S, Matsushima K: Intervention of MadCAM-1 or fractalkine alleviates graft-versus-host reaction associated intestinal injury while preserving graft-versus-tumor effects. *Journal of leukocyte biology* 2007, 81(1):176-185.
12. Sandborn W J, Hanauer S B, Katz S, Safdi M, Wolf D G, Baerg R D, Tremaine W J, Johnson T, Diehl N N, Zinsmeister A R: Etanercept for active Crohn's disease: a randomized, double-blind, placebo-controlled trial. *Gastroenterology* 2001, 121(5):1088-1094.

What is claimed is:

1. A mutant of tumor necrosis factor receptor 1B (TNFR-1B) (SEQ ID NO:3) that modulates the binding of TNFR-1B to one or more of tumor necrosis factor receptor alpha (TNFα), inducible costimulatory ligand (ICOS-L), and mucosal vascular addressing cell adhesion molecule 1 (MadCAM-1), wherein the mutant is selected from the group consisting of mutants K42D, T48A, N171D, S79D, R113D, L114A, R119D, K120D, D58A, R19D, S59D, L64D, R77A, S107D, R119A, K120A, R129A, V138D, K140A, 1156D, 1168D, N171A and M174D, wherein mutant numbering is based on the mature form of TNFR-1B in which the signal peptide at residues 1-22 has been removed.

2. The mutant of claim 1, selected from the group consisting of mutants K42D, T48A and N171D that, compared to TNFR-1B, have reduced binding to TNFα, ICOS-L and MadCAM-1.

3. The mutant of claim 1, selected from the group consisting of mutants S79D, R113D, L114A, R119D and K120D that, compared to TNFR-1B, have reduce binding to ICOS-L and MadCAM-1, but not to TNFα.

4. The mutant of claim 1, which is mutant D58A that, compared to TNFR-1B, has reduced binding to TNFα and ICOS-L, but not to MadCAM-1.

5. The mutant of claim 1, selected from the group consisting of mutants R19D, S59D, L64D, R77A, S107D, R119A, K120A, R129A, V138D, K140A, 1156D, 1168D, N171A and M174D that, compared to TNFR-1B, predominately reduce binding to MadCAM-1.

6. A fusion protein comprising the mutant of claim 1 and an immunoglobulin Fc sequence.

7. The fusion protein of claim 6, wherein the immunoglobulin is an IgG.

8. The fusion protein of claim 6, wherein the immunoglobulin is IgG1.

9. A pharmaceutical composition comprising the fusion protein of claim 6 and a pharmaceutically acceptable carrier.

10. A method for screening for a candidate compound for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis and inflammatory bowel disease, the method comprising testing the compound to determine if the compound modulates the interaction between one or more of TNFR-1B and ICOS-L, TNFR-1B and MadCAM-1, and TNFR-1B and ISLR2, wherein a compound that is tested and determined to modulate the interaction between one or more of TNFR-1B and ICOS-L, TNFR-1B and MadCAM-1, or TNFR-1B and ISLR2 is a candidate compound for treating a disease or disorder selected from the group consisting of rheumatoid arthritis, psoriatic arthritis, ankylosing spondylitis, plaque psoriasis, juvenile idiopathic arthritis, inflammation, autoimmune disease, immune disorder, Crohn's disease, ulcerative colitis and inflammatory bowel disease.

11. The method of claim 10, wherein binding between TNFR-1B and ICOS-L, TNFR-1B and MadCAM-1, and/or TNFR-1B and ISLR2 is determined in the presence of the candidate compound and in the absence of the candidate compound, and wherein a change in the binding between TNFR-1B and ICOS-L, TNFR-1B and MadCAM-1, and/or TNFR-1B and ISLR2 in the presence of the candidate compound indicates that the candidate compound modulates the interaction between TNFR-1B and ICOS-L, TNFR-1B and MadCAM-1, and/or TNFR-1B and ISLR2.

12. The method of claim 10, wherein the compound is a non-naturally occurring small molecule of 2,000 daltons or less, or an antibody or an antibody fragment.

* * * * *